(12) United States Patent
Sapiro et al.

(10) Patent No.: US 11,158,403 B1
(45) Date of Patent: Oct. 26, 2021

(54) METHODS, SYSTEMS, AND COMPUTER READABLE MEDIA FOR AUTOMATED BEHAVIORAL ASSESSMENT

(71) Applicant: Duke University, Durham, NC (US)

(72) Inventors: Guillermo Sapiro, Durham, NC (US); Helen Egger, Durham, NC (US); Geraldine Dawson, Durham, NC (US); Robert Calderbank, Durham, NC (US); Jeffrey Baker, Durham, NC (US); Kimberly Carpenter, Chapel Hill, NC (US); Adrianne Harris, Chapel Hill, NC (US); Kathleen Campbell, Durham, NC (US); Jordan Hashemi, Durham, NC (US); Qiang Qiu, Durham, NC (US); Mariano Tepper, Durham, NC (US)

(73) Assignee: Duke University, Durham, NC (US)

(*) Notice: Subject to any disclaimer, the term of this patent is extended or adjusted under 35 U.S.C. 154(b) by 1046 days.

(21) Appl. No.: 15/141,391

(22) Filed: Apr. 28, 2016

Related U.S. Application Data

(60) Provisional application No. 62/154,483, filed on Apr. 29, 2015.

(51) Int. Cl.
*G16H 10/60* (2018.01)
*G16H 50/20* (2018.01)

(52) U.S. Cl.
CPC .............. *G16H 10/60* (2018.01); *G16H 50/20* (2018.01)

(58) Field of Classification Search
CPC ................................ G16H 10/60; G16H 50/20
See application file for complete search history.

(56) References Cited

U.S. PATENT DOCUMENTS

| | | | |
|---|---|---|---|
| 9,530,080 B2 | 12/2016 | Glazer | |
| 10,165,176 B2 | 12/2018 | Frahm et al. | |
| 2004/0210159 A1* | 10/2004 | Kibar | A61B 5/4803 |
| | | | 600/558 |
| 2008/0227063 A1* | 9/2008 | Kenedy | G16H 50/30 |
| | | | 434/219 |

(Continued)

OTHER PUBLICATIONS

Peng Wang, Christian Kohler, Fred Barrett, Raquel Gur, Ruben Gur, Ragini Verma, "Quantifying Facial Expression Abnormality in Schizophrenia by Combining 2D and 3D Features" IEEE, 2007 (Year: 2007).*

(Continued)

*Primary Examiner* — Jonathan Durant
*Assistant Examiner* — Gregory D. Moseley
(74) *Attorney, Agent, or Firm* — Jenkins, Wilson, Taylor & Hunt, P.A.

(57) ABSTRACT

The subject matter described herein includes methods, systems, and computer readable media for automated behavioral assessment. According to one aspect, a method for automated behavioral assessment is provided. The method occurs at a computing platform including a processor and memory. The method includes providing at least one stimulus for eliciting a response from a user. The method also includes obtaining, using a camera or sensor communicatively coupled to the computing platform, the at least one response. The method also includes determining, using the at least one response, a behavioral assessment associated with the user.

23 Claims, 8 Drawing Sheets

(56) References Cited

U.S. PATENT DOCUMENTS

| | | | |
|---|---|---|---|
| 2012/0293773 A1* | 11/2012 | Publicover | A61B 3/113 351/210 |
| 2012/0314045 A1 | 12/2012 | Billard et al. | |
| 2014/0153794 A1 | 6/2014 | Varaklis et al. | |
| 2014/0315168 A1* | 10/2014 | Movellan | A61B 5/165 434/236 |
| 2015/0099946 A1* | 4/2015 | Sahin | A61B 5/16 600/301 |
| 2015/0282705 A1* | 10/2015 | Avital | A61B 3/113 600/301 |
| 2015/0288877 A1 | 10/2015 | Glazer | |
| 2016/0128617 A1 | 5/2016 | Morris et al. | |
| 2016/0309081 A1 | 10/2016 | Frahm et al. | |
| 2017/0046567 A1 | 2/2017 | Hong et al. | |
| 2018/0098724 A1* | 4/2018 | Lu | A61B 5/7264 |

OTHER PUBLICATIONS

Aharon, et al., "K-SVD: An Algorithm for Designing Overcomplete Dictionaries for Sparse Representation," IEEE Trans Signal Process, vol. 54, No. 11, pp. 4311-4322 (2006).

Arvin, M., "Navy Funds Autism-Screening App, Hoping for Help with PTSD", Artificial Intelligence Online. pp. 1-6 (Mar. 20, 2016).

Bryson et al, "A prospective case series of high-risk infants who developed autism," (SpringerLink) Journal of Autism and Developmental Disorders, vol. 37, No. 1, pp. 12-24 (2007).

Bryson, et al., "The autism observation scale for infants: scale development and reliability data," (SpringerLink) Journal of Autism and Developmental Disorders, vol. 38, No. 4, pp. 731-738 (25 pages) (2008).

Dalal, et al, "Histograms of oriented gradients for human detection," Proceedings of the IEEE Computer Society Conference on Computer Vision and Pattern Recognition (CVPR '05), pp. 886-893, San Diego, USA, pp. 1-9 (Jun. 2005).

Dawson, G., "Early behavioral intervention, brain plasticity, and the prevention of autism spectrum disorder," Development and Psychopathology, vol. 20, No. 3, pp. 775-803 (2008).

Elsabbagh, et al., "Visual orienting in the early broader autism phenotype: disengagement and facilitation," Journal of Child Psychology and Psychiatry and Allied Disciplines, vol. 50, No. 5, pp. 637-642 (2009).

Elsabbagh, et al., "Disengagement of Visual Attention in Infancy is Associated with Emerging Autism in Toddlerhood," Biological Psychiatry, vol. 74, no1. 3, pp. 189-194 (2013).

Howard, et al., "A comparison of intensive behavior analytic and eclectic treatments for young children with autism," Research in Developmental Disabilities, vol. 26, No. 4, pp. 359-383 2005.

Jones, et al., "Absence of Preferential Looking to the Eyes of Approaching Adults Predicts Level of Social Disability in 2-Year-Old Toddlers with Autism Spectrum Disorder," Archives of General Psychiatry, vol. 65, No. 8, pp. 946-954 (2008).

Kalal, et al., "Face-TLD: Tracking-Learning-Detection Applied to Faces," Proceedings of 2010 IEEE 17th International Conference on Image Processing (ICIP '10), Hong Kong, pp. 3789-3792 (Sep. 2010).

Klin, et al., "Visual Fixation Patterns During Viewing of Naturalistic Social Situations as Predictors of Social Competence in Individuals with Autism," Archives of General Psychiatry, vol. 59, No. 9, pp. 809-816 (Sep. 2002).

Landry, et al., "Impaired disengagement of attention in young children with autism," Journal of Child Psychology and Psychiatry and Allied Disciplines, vol. 45, No. 6, pp. 1115-1122 (2004).

Moore, et al., "Local binary patterns for Multiview facial expression recognition," Computer Vision and Image Understanding, vol. 115, pp. 541-558 (2011).

Nichols, et al, "Social Smiling and its Components in High-risk Infant Siblings Without Later ASD Symptomatology," J Autism Dev Disord, vol. 44, No. 4, pp. 894-902 (2014).

Osterling, et al, "Early recognition of children with autism: a study of first birthday home videotapes," Journal of Autism and Developmental Disorders, vol. 24, No. 3, pp. 247-257 (1994).

Ozonoff, et al, "A Prospective Study of the Emergence of Early Behavioral Signs of Autism", J Am Acad Child Adolesc Psychiatry, vol. 49, No. 3, pp. 256-266 (Mar. 2010).

Sandbach, et al, "Static and dynamic 3D facial expression recognition: A comprehensive survey," Image and Vision Computing, vol. 30, No. 10, pp. 683-697 (2012).

Scott, E., "App aims for faster autism diagnosis," The Arizona Republic, pp. 1-3 (Apr. 13, 2013).

Shan, et al, "Facial expression recognition based on local binary patterns: a comprehensive study," Image and Vision Computing, vol. 27, pp. 803-816 (2009).

Wright, et al, "Robust face recognition via sparse representation," IEEE Transactions on Pattern Analysis (PAMI), vol. 31, No. 2, pp. 1-18 (2009).

Yandell, K., "Computer vision may aid in screening for autism," SFARI Simons Foundation Autism Research Initiative, p. 1 (Jul. 16, 2014).

Zeng, et al, "A Survey of Affect Recognition Methods: Audio, Visual, and Spontaneous Expressions," IEEE Transactions on Pattern Analysis and Machine Intelligence (PAMI), vol. 31, No. 1, pp. 39-58 (Jan. 2009).

Zhao, et al, "A unified probabilistic framework for automatic 3D facial expression analysis based on a bayesian belief inference and statistical feature models," Image and Vision Computing, vol. 31, No. 3, pp. 231-245 (2013).

Adrien et al., "Autism and family home movies: preliminary findings," Journal of Autism and Developmental Disorders, vol. 21(1), pp. 43-49, (1991).

Adrien et al., "Early symptoms in autism from family home movies. Evaluation and comparison between 1st and 2nd year of life using I.B.S.E. scale," Acta Paedopsychiatrica, vol. 55, No. 2, pp. 71-75, (1992).

Baranek, G.T., "Autism during infancy: a retrospective video analysis of sensory-motor and social behaviors at 9-12 months of age," Journal of Autism and Developmental Disorders, vol. 29, No. 3, pp. 213-224 (1999).

Bloch et al., "On the onset of eye-head coordination in infants," Behavioural Brain Research, vol. 49, No. 1, pp. 85-90 (1992).

Boujarwah, et al., "Understanding the challenges and opportunities for richer descriptions of stereotypical behaviors of children with ASD: a concept exploration and validation," Proceedings of the 12th International ACM SIGACCESS Conference on Computers and Accessibility (ASSETS '10), pp. 67-74, Orlando, Fla, USA (Oct. 2010).

Chang, et al, "LIBSVM: a library for support vector machines," ACM Trans Intelligent Systems and Technology, vol. 2, No. 3, pp. 1-39 (2011).

Downing, et al., "Can the AOSI at nine months discriminate between infants at high or low risk for ASD?", International Meeting for Autism Research (IMFAR '11), San Diego, Calif, USA (2011).

Esposito, et al., "Analysis of unsupported gait in toddlers with autism," Brain and Development, vol. 33, No. 5, pp. 367-373 (2011).

Everingham, et al., ""Hello! My name is . . . Buffy"—automatic naming of characters in TV video," Proceedings of the British Machine Vision Conference (BMVC '06), Edinburgh, UK (2006).

Li, et al, "Learning to predict gaze in egocentric video," Proceedings of the International Conference on Computer Vision (ICCV '13), Sydney, Australia (2013).

Freeth, et al., "The Influence of visual saliency on fixation patterns in individuals with autism spectrum disorders," Neuropsychologia, vol. 49, No. 1, pp. 156-160 (2011).

Goodwin, et al., "Automated detection of stereotypical motor movements," Journal of Autism and Developmental Disorders, vol. 41, No. 6, pp. 770-782 (2011).

Gross, et al, "Multi-PIE," FG, 2010, pp. 807-813.

Guney, et al, "Cross-pose facial expression recognition," FG, pp. 1-6 (2013).

(56) References Cited

OTHER PUBLICATIONS

Hastie, et al, "The Elements of Statistical Learning", Springer-Verlag (2009).
Kumano, et al, "Pose-invariant facial expression recognition using variable intensity templates," IJVC, vol. 83, No. 2, pp. 178-194 (2009).
Losche, et al, "Sensorimotor and action development in autistic children from infancy to early childhood," Journal of Child Psychology and Psychiatry and Allied Disciplines, vol. 31, No. 5, pp. 749-761 (1990).
Robins et al., "Modified Checklist for Autism in Toddlers, Revised with Follow-Up (M-Chat-R/F)TM," www.mchatscreen.com, pp. 1-3 (2009).
Muratori, et al, "Early signs of autism in the first year of life," in Signs of Autism in Infants: Recognition and Treatment, pp. 46-62, Karnac, London, UK (2007).
Murphy-Chutorian, et al, "Head pose estimation in computer vision: a survey," PAMI, vol. 31, No. 4, pp. 607-626 (2009).
Nadig, et al., "A prospective study of response to name in infants at risk for autism," Archives of Pediatrics and Adolescent Medicine, vol. 161, No. 4, pp. 378-383 (2007).
Rehg, et al, "Decoding children's social behavior," CVPR, pp. 3414-3421 (2013).
Rodier, et al, "Converging evidence for brain stem injury in autism," Development and Psychopathology, vol. 14, No. 3, pp. 537-557 (2002).
Shattuck, et al, "Timing of identification among children with an autism spectrum disorder: findings from a population-based surveillance study," Journal of the American Academy of Child and Adolescent Psychiatry, vol. 48, No. 5, pp. 474-483 (2009).
Tang, et al, "Non-frontal view facial expression recognition based on ergodic hidden markov model supervectors," in ICME, pp. 1202-1207 (2010).
Tepper, et al, "Decoupled coarse-to-fine matching and nonlinear regularization for efficient motion estimation," in Proceedings of the 19th IEEE International Conference on Image Processing (ICIP '12), pp. 1517-1520, Orlando, Fla, USA (Oct. 2012).
Vatahska, et al, "Feature-based head pose estimation from images," in Proceedings of the 7th IEEE-RAS International Conference on Humanoid Robots (HUMANOIDS '07), pp. 330-335, Pittsburgh, PA, USA (Dec. 2007).
Xiong, et al, "Supervised descent method and its applications to face alignment," CVPR, pp. 532-539, (2013).
Ye, Z., et al., "Detecting eye contact using wearable eye-tracking glasses," in Proceedings of the 14th International Conference on Ubiquitous Computing (UbiComp '12), pp. 699-704, Pittsburgh, Pa, USA (Sep. 2012).
Yin, et al, "A 3D facial expression database for facial behavior research," in FG, pp. 211-216 (2006).
Zhu, Z., et al, "Robust real-time face pose and facial expression recovery," CVPR, pp. 681-688, (2006).
Zwaigenbaum, et al, "Behavioral manifestations of autism in the first year of life," International Journal of Developmental Neuroscience, vol. 23, No. 2-3, pp. 143-152 (2005).
Hashemi, et al, "Computer vision tools for low-cost and non-invasive measurement of autism-related behaviors in infants," Autism Research and Treatment (2014).
Hashemi, et al., "A computer vision approach for the assessment of autism-related behavioral markers," IEEE International Conference on Development and Learning and Epigenetic Robotics (ICDL), San Diego, CA, 2012, pp. 1-7 (2012).
Mannan, et al, "Automatic control of saccadic eye movements made in visual inspection of briefly presented 2-D images," Spatial vision, vol. 9, No. 3, pp. 363-386 (1995).
Qiu, et al, "Domain adaptive dictionary learning," in ECCV, pp. 631-645 (2012).
Rudovic, et al, "Coupled Gaussian processes for pose-invariant facial expression recognition," PAMI, vol. 35, No. 6, pp. 1357-1369 (2013).
Taheri, et al, "Structure-preserving sparse decomposition for facial expression analysis," IEEE Trans Image Process, vol. 23, No. 8, pp. 1-12 (2013).
Jones et al., "Attention to Eyes is Present but in Decline in 2-6 Month-Olds Later Diagnosed with Autism," Nature, vol. 504, pp. 427-431 (2013).
Campbell et al. "Use of a Digital Modified Checklist for Autism in Toddlers—Revised with Follow-up to Improve Quality of Screening for Autism," The Journal of Pediatrics, vol. 183, pp. 133-139 (2017).
Campbell et al. "Computer vision analysis captures atypical attention in toddlers with autism," Autism, vol. 23(3), pp. 619-628 (2018).
Chang et al. "Synthesis-based Low-cost Gaze Analysis," International Conference on Human-Computer Interaction, pp. 1-6, Jul. 2016.
Chawarska et al. "Decreased Spontaneous Attention to Social Scenes in 6-Month-Old Infants Later Diagnosed with Autism Spectrum Disorders," Biological Psychiatry, No. 74(3), pp. 195-203 (2013).
Dawson et al. "Children with Autism Fail to Orient to Naturally Occurring Social Stimuli," Journal of Autism and Developmental Disorders, vol. 28, No. 6, pp. 479-485 (1998).
De la Torre et al., "IntraFace," Author manuscript, pp. 1-30 [published in final edited form as: IEEE Int Conf Autom Face Gesture Recognit Workshops] (2015).
Esposito et al. "An exploration of symmetry in early autism spectrum disorders: Analysis of lying," Brain Dev, 31(2), pp. 131-138 (2009).
Fischler et al. "Random Sample Consensus: A Paradigm for Model Fitting with Applications to Image Analysis and Automated Cartography," Commun. ACM, vol. 24, No. 6, pp. 381-395 (1981).
Ghanouni et al. "Effect of Social Stimuli on Postural Responses in Individuals with Autism Spectrum Disorder," J Autism Dev Disord, 47(5), pp. 1305-1313 (2017).
Gima et al. "Early motor signs of autism spectrum disorder in spontaneous position and movement of the head," Exp Brain Res, 236(4), pp. 1139-1148 (2018).
Gotham et al. "The Autism Diagnostic Observation Schedule: Revised Algorithms for Improved Diagnostic Validity," Journal of Autism and Developmental Disorders, 37(4), pp. 613-627 (2007).
Hashemi et al. "Computer Vision Analysis for Quantification of Autism Risk Behaviors," IEEE Transactions on Affective Computing, pp. 1-12 (2018).
Heiser et al. "Objective measurement of hyperactivity, impulsivity, and inattention in children with hyperkinetic disorders before and after treatment with methylphenidate," Eur Child Adolesc Psychiatry, 13(2), pp. 100-104 (2004).
Hytönen et al. "Postural Control and Age," Acta Otolaryngol, 113(2), pp. 119-122 (1993).
Kirchner et al. "Autistic Symptomatology, Face Processing Abilities, and Eye Fixation Patterns," Journal of Autism and Developmental Disorders, 41(2), pp. 158-167 (2011).
Lim et al. "Effect of Visual Information on Postural Control in Adults with Autism Spectrum Disorder," J Autism Dev Disord, 49, pp. 4731-4739 (2019).
Reiersen et al. "Co-occurrence of Motor Problems and Autistic Symptoms in Attention-Deficit/Hyperactivity Disorder," J Am Acad Child Adolesc Psychiatry, 47(6), pp. 662-672 (2008).
Merin et al. "Visual Fixation Patterns during Reciprocal Social Interaction Distinguish a Subgroup of 6-Month-Old Infants At-Risk for Autism from Comparison Infants," J Autism Dev Disord, 37, pp. 108-121 (2007).
Minshew et al. "Underdevelopment of the postural control system in autism," Neurology, 63(11), pp. 2056-2061 (2004).
Morris et al. "Differences in the use of vision and proprioception for postural control in autism spectrum disorder," Neuroscience, 307, pp. 273-280 (2015).
Murias et al. "Validation of Eye-Tracking Measures of Social Attention as a Potential Biomarker for Autism Clinical Trials," Autism Res., No. 11(1), pp. 166-174 (2018a).

(56) References Cited

OTHER PUBLICATIONS

Norbury et al. "Eye-movement patterns are associated with communicative competence in autistic spectrum disorders," Journal of Child Psychology and Psychiatry, 50(7), pp. 834-842 (2009).
Pelphrey et al. "Visual Scanning of Faces in Autism," Journal of Autism and Developmental Disorders, vol. 32, No. 4, pp. 249-261 (2002).
Swettenham et al. "The Frequency and Distribution of Spontaneous Attention Shifts between Social and Nonsocial Stimuli in Autistic, Typically Developing, and Nonautistic Developmentally Delayed Infants," Journal of Child Psychology and Psychiatry, vol. 39, No. 5, pp. 747-753 (1998).
Werner et al. "Brief Report: Recognition of Autism Spectrum Disorder Before One Year of Age: A Retrospective Study Based on Home Videotapes," Journal of Autism and Developmental Disorders, vol. 30, No. 2, pp. 157-162 (2000).
Anzulewicz et al. "Toward the Autism Motor Signature: Gesture patterns during smart tablet gameplay identify children with autism," Sci Rep, vol. 6, pp. 31107-1-31107-13 (2016).
Baltrusaitis et al. "Openface: An open source facial behavior analysis toolkit," IEEE Winter Conference on Applications of Computer Vision (WACV), p. 1-10 (2016).
Baltrusaitis et al. "Openface 2.0: Facial Behavior Analysis Toolkit," IEEE International Conference on Automatic Face and Gesture Recognition (2018).
Baveye et al. "LIRIS-ACCEDE: A Video Database for Affective Content Analysis," IEEE Transactions on Affective Computing, vol. 6, pp. 43-55, 2015.
Brisson et al. "Motor anticipation failure in infants with autism: a retrospective analysis of feeding situations," Autism, 16(4), pp. 420-429 (2012).
Campbell et al. "Computer Vision Analysis Captures Atypical Attention in Toddlers with Autism," Author manuscript, pp. 1-19 [Published in final edited form as: Autism, 23(3), pp. 619-628 (2019)].
"Computer vision of facial dynamics in infants at risk for autism," Job offer listed on Euraxess, pp. 1-4 (2017) [Accessed online Aug. 14, 2020].
Commonly-assigned, Co-pending U.S. Appl. No. 16/678,789 for "Methods, Systems, and Computer Readable Media for Automated Attention Assessment," (Unpublished, filed Nov. 8, 2019).
Commonly-assigned, Co-pending U.S. Appl. No. 16/678,828 for "Methods, Systems, and Computer Readable Media for Conducting an Automatic Assessment of Postural Control of a Subject," (Unpublished, filed Nov. 8, 2019).
Constantino et al. "Infant viewing of social scenes is under genetic control and is atypical in autism," Author manuscript, pp. 1-41 [Published in final edited form as: Nature, vol. 547(7663), pp. 340-344, (2017)].
Cook et al. "Atypical basic movement kinematics in autism spectrum conditions," Brain, 136(Pt 9), pp. 2816-2824 (2013).
Dawson et al. "Case Study of the Development of an Infant with Autism from Birth to Two Years of Age," Author manuscript, pp. 1-14 [Published in final edited form as: J Appl Dev Psychol, 21(3), pp. 299-313 (2000)].
Dawson, K. Toth, R. Abbott, et al., "Early Social Attention Impairments in Autism: Social Orienting, Joint Attention, and Attention to Distress," Developmental Psychology, No. 40(2), pp. 271-283 (2004).
Dementhon et al. "Model-Based Object Pose in 25 Lines of Code," International Journal of Computer Vision, 15(1), pp. 123-141 (1995).
Egger, et al. "Automatic emotion and attention analysis of young children at home: A ResearchKit autism feasibility study," npj Nature Digital Medicine, 20, pp. 1-10 (2018).
Esler et al. "The Autism Diagnostic Observation Schedule, Toddler Module: Standardized Severity Scores," Author manuscript, pp. 1-28, [Published in final edited form as J Autism Dev Disord, vol. 45(9), pp. 2704-2720 (2015)].
Flanagan et al. "Head Lag in Infants at Risk for Autism: A Preliminary Study," Am J Occup Ther, 66(5), pp. 577-585 (2012).
Gouleme et al. "Postural Control and Emotion in Children with Autism Spectrum Disorders," Transl Neurosci, 8, pp. 158-166 (2017).
Hashemi et al. "A scalable app for measuring autism risk behaviors in young children: A technical validity and feasibility study," MobiHealth, pp. 1-5 (2015).
Jeni et al. "Dense 3D Face Alignment from 2D Videos in Real-Time," 2015 11th IEEE International Conference and Workshops on Automatic Face and Gesture Recognition (FG), pp. 1-8, May 4-8, 2015, DOI: 10.1109/FG.2015.7163142, Date Added to IEEE Xplore: Jul. 23, 2015.
Jeni et al. "Person-Independent 3D Gaze Estimation Using Face Frontalization," 2016 IEEE Conference on Computer Vision and Pattern Recognition Workshops (CVPRW) DOI: 10.1109/CVPRW.2016.104.
Jones et al. "Reduced engagement with social stimuli in 6-month-old infants with later autism spectrum disorder: A longitudinal prospective study of infants at high familial risk," Journal of Neurodevelopmental Disorders, 8:7, pp. 1-20 (2016).
Kang et al. "Automated Tracking and Quantification of Autistic Behavioral Symptoms Using Microsoft Kinect," Stud Health Technol Inform, 220, pp. 167-170 (2016).
Klin et al. "Social visual engagement in infants and toddlers with autism: Early developmental transitions and a model of pathogenesis," Author manuscript, pp. 1-34 [Published in final edited form as: Neurosci Biobehav Rev., No. 50, pp. 189-203 (2014)].
Lucas da Silva et al. "A Web-Based Application to Address Individual Interests of Children with Autism Spectrum Disorders," Procedia Computer Science, vol. 14, pp. 20-27, (2012).
Lucas da Silva et al. "Inducing behavior change in children with Autism Spectrum Disorders by monitoring their attention," Proceedings of the International Conference on Physiological Computing Systems, vol. 1, pp. 131-136 (2014).
Rice et al. "Parsing Heterogeneity in Autism Spectrum Disorders: Visual Scanning of Dynamic Social Scenes in School-Aged Children," Author manuscript, pp. 1-17 [Published in final edited form as J Am Acad Child Adolesc Psychiatry, 51(3), pp. 238-248 (2012)].
Robins et al. "Validation of the Modified Checklist for Autism in Toddlers, Revised with Follow-up (M-CHAT-R/F)," Pediatrics, No. 133(1), pp. 37-45 (2014).
Rudovic et al., "Personalized machine learning for robot perception of affect and engagement in autism therapy," Science Robotics, vol. 3:19, pp. 1-11 (2018).
Martin et al. "Objective measurement of head movement differences in children with and without autism spectrum disorder," Mol Autism, 9:14, pp. 1-10 (2018).
Marko et al. "Behavioural and neural basis of anomalous motor learning in children with autism," Brain, 138 (Pt 3): pp. 784-797 (2015).
Metallinou et al. "Quantifying Atypicality in Affective Facial Expressions of Children With Autism Spectrum Disorders," Author Manuscript, pp. 1-12 [Published in final edited form as Proc (IEEE Int Conf Multimed Expo), 1-6 (2013)].
Murias et al. "Electrophysiological Biomarkers Predict Clinical Improvement in an Open-Label Trial Assessing Efficacy of Autologous Umbilical Cord Blood for Treatment of Autism," Stem Cells Translational Medicine, 7, pp. 783-791 (2018).
Owada et al. "Computer-analyzed facial expression as a surrogate marker for autism spectrum social core symptoms," Plos One, 13(1), pp. 1-16 (2018).
Pierce et al. "Preference for Geometric Patterns Early in Life as a Risk Factor for Autism," Author manuscript, pp. 1-20 [Published in final edited form as: Archives of General Psychiatry, No. 68(1), pp. 101-109 (2011)].
Qiu et al. "Low-cost Gaze and Pulse Analysis using RealSense," MobiHealth, pp. 1-4 (2015).
Shi et al. "Different Visual Preference Patterns in Response to Simple and Complex Dynamic Social Stimuli in Preschool-Aged Children with Autism Spectrum Disorders," PLOS One, No. 10(3), pp. 1-16 (2015).
Shic et al., "Limited Activity Monitoring in Toddlers with Autism Spectrum Disorder," Author manuscript, pp. 1-19 [Published in final edited form as: Brain Research, No. 1380, pp. 246-254 (2011)].

(56) References Cited

OTHER PUBLICATIONS

Silva et al. "Automated Evaluation System for Human Pupillary Behavior," Stud Health Technol Inform. 245, pp. 589-593 (2017).
Steakley, "Using Kinect cameras to automate autism diagnosis," Scope, scopeblog.stanford.edu, pp. 1-4 (2012) [Accessed online Aug. 14, 2020].
Tassi, "Microsoft's Kinect Being Employed to Help Detect Autism Early," Forbes.com, pp. 1-3 (2012) [Accessed online Aug. 14, 2020].
Teitelbaum et al. "Movement analysis in infancy may be useful for early diagnosis of autism," Proc Natl Acad Sci USA, vol. 95(23), pp. 13982-13987 (1998).
Wu et al. "A Biomarker Characterizing Neurodevelopment with applications in Autism," Scientific reports, 8:614, pp. 1-14 (2018).
Zappella et al. "What do home videos tell us about early motor and socio-communicative behaviours in children with autistic features during the second year of life—An exploratory study," Author Manuscript, pp. 1-18 [Published in final edited form as: Early Hum Dev, 91(10), pp. 569-575 (2015)].

* cited by examiner

METHODS, SYSTEMS, AND COMPUTER READABLE MEDIA FOR AUTOMATED BEHAVIORAL ASSESSMENT

CROSS REFERENCE TO RELATED APPLICATIONS

This application claims the benefit of U.S. Provisional Patent Application Ser. No. 62/154,483, filed Apr. 29, 2015, the disclosure of which is incorporated herein by reference in its entirety.

GOVERNMENT INTEREST

This invention was made with government support under Grant No. 1028076 awarded by the National Science Foundation. The government has certain rights in the invention.

TECHNICAL FIELD

The subject matter described herein relates generally to automated behavioral assessment. More particularly, the subject matter described herein includes methods, systems, and computer readable media for automated behavioral assessment.

BACKGROUND

Behavioral disorders affect many people throughout the world. Current estimates indicate that 1 in 9 children may have or develop a mental health and/or behavior disorder, such as autism, an anxiety disorder, an aggressiveness disorder, or attention deficit and hyperactivity disorder (ADHD). Research has shown that treatments for various behavioral disorders, including autism, can be more effective when diagnosed and treated early. Moreover, early intervention and consistent monitoring can be useful for tracking individual progress and may also be useful for understanding subjects in clinical trials. However, many children are not diagnosed as early as possible and/or do not receive adequate care after diagnosis. For example, the average age of autism diagnosis is 5.3 years old in the United States, yet autism may be detected as early as 18 months.

In spite of the significant recent advances in the genetics and neuroscience, behavioral observation and coding is still the gold standard in screening, diagnosis, and outcome assessment, and will continue being so in the foreseeable future. Current behavioral assessment techniques generally require trained clinicians and/or expensive equipment and can be very time intensive. Hence, current behavioral assessment techniques include barriers for early diagnosis and monitoring of many behavioral disorders. Monitoring those that exhibit symptoms of behavior issues can be very beneficial both for intervention evaluation and for assessing longitudinal changes, which is important for proper evaluation. However, such monitoring invokes significant a time burden and, as such, is virtually impossible with current standard clinical practice.

Accordingly, a need exists for methods, systems, and computer readable media for automated behavioral assessment.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

The subject matter described herein includes methods, systems, and computer readable media for automated behavioral assessment. According to one aspect, a method for automated behavioral assessment is provided. In some embodiments, the method occurs at a computing platform including a processor and memory. In some embodiments, the method includes providing at least one stimulus for eliciting a response from a user. In some embodiments, the method also includes obtaining, using a camera or sensor communicatively coupled to the computing platform, the at least one response. In some embodiments, the method also includes determining, using the at least one response, a behavioral assessment associated with the user.

A system for automated behavioral assessment is also disclosed. In some embodiments, the system includes a computing platform including a processor and memory. In some embodiments, the computing platform includes a behavioral assessment module (BAM) configured to provide at least one stimulus for eliciting a response from a user, to obtain, using a camera or sensor communicatively coupled to the computing platform, the at least one response, and to determine, using the at least one response, a behavioral assessment associated with the user.

The subject matter described herein may be implemented in software in combination with hardware and/or firmware. For example, the subject matter described herein may be implemented in software executed by a processor (e.g., a hardware-based processor). In one exemplary implementation, the subject matter described herein may be implemented using a non-transitory computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, such as field programmable gate arrays, and application specific integrated circuits. In addition, a computer readable medium that implements the subject matter described herein may be located on a single device or computing platform or may be distributed across multiple devices or computing platforms.

As used herein, the term "node" refers to a physical computing platform including one or more processors and memory.

As used herein, the terms "function" or "module" refer to software in combination with hardware and/or firmware for implementing features described herein. In some embodiments, a module may include a field-programmable gateway array (FPGA), an application-specific integrated circuit (ASIC), or a processor.

BRIEF DESCRIPTION OF THE DRAWINGS

The subject matter described herein will now be explained with reference to the accompanying drawings of which.

DETAILED DESCRIPTION

The subject matter described herein discloses methods, systems, and computer readable media for automated behavioral assessment. As used herein, the term "behavioral assessment" refers to analyzing behavior related information, e.g., performing behavioral coding associated with user responses, and/or providing an assessment based at least in part on the behavior related information. Aspects of the present subject matter described herein perform automated behavioral assessment. In some embodiments, automated behavioral assessment may include behavioral analysis (e.g., identifying and/or coding of user responses into quantitative metrics) and may occur at or be performed by an application (also referred to herein as "app") executing on a mobile device (e.g., a smartphone or a tablet device) or other computer (e.g., a server or computerized health related equipment).

In accordance with some aspects of the present subject matter, automated behavioral assessment and/or automated behavioral analysis may be performed by one or more computing platforms. For example, a smartphone containing a camera may be usable to execute a behavioral assessment app that can provide stimuli, such as via a short (e.g., six minute) video, and can record user responses to the stimuli via the camera. In this example, the app or another entity (e.g., a communicatively coupled server) may be configured to process and/or analyze recorded responses and/or other information, e.g., by identifying facial expressions in recorded responses and scoring or coding the facial expressions into quantitative metrics. Continuing with this example, a behavioral assessment may be determined using the recorded responses and/or other information by determining whether the user responses and/or quantitative metrics associated with the user responses are indicative of one or more behavior disorders.

By providing techniques, mechanisms, and/or methods for automated behavioral assessments, diagnosis and/or treatment for various behavioral disorders (e.g., autism, an anxiety disorder, an aggressiveness disorder, or attention deficient and hyperactivity disorder (ADHD)) may be performed quickly and efficiently. Moreover, by providing automated behavioral assessments using software executing on mobile devices or other relatively inexpensive devices, cost barriers associated with diagnosis and/or treatment of behavioral disorders may be alleviated. Further, using aspects of the present subject matter, diagnosis and/or treatment for many behavioral disorders in young children (e.g., ages 1-5) may be facilitated and/or improved over conventional methods, thereby allowing treatments, strategies, and/or intervention methods to be implemented more broadly and earlier than previously possible with conventional methods. Moreover, using aspects of the present subject matter, consistency of assessment may be improved over conventional methods, e.g., by utilizing automated techniques and precise measurements.

Figure 1:
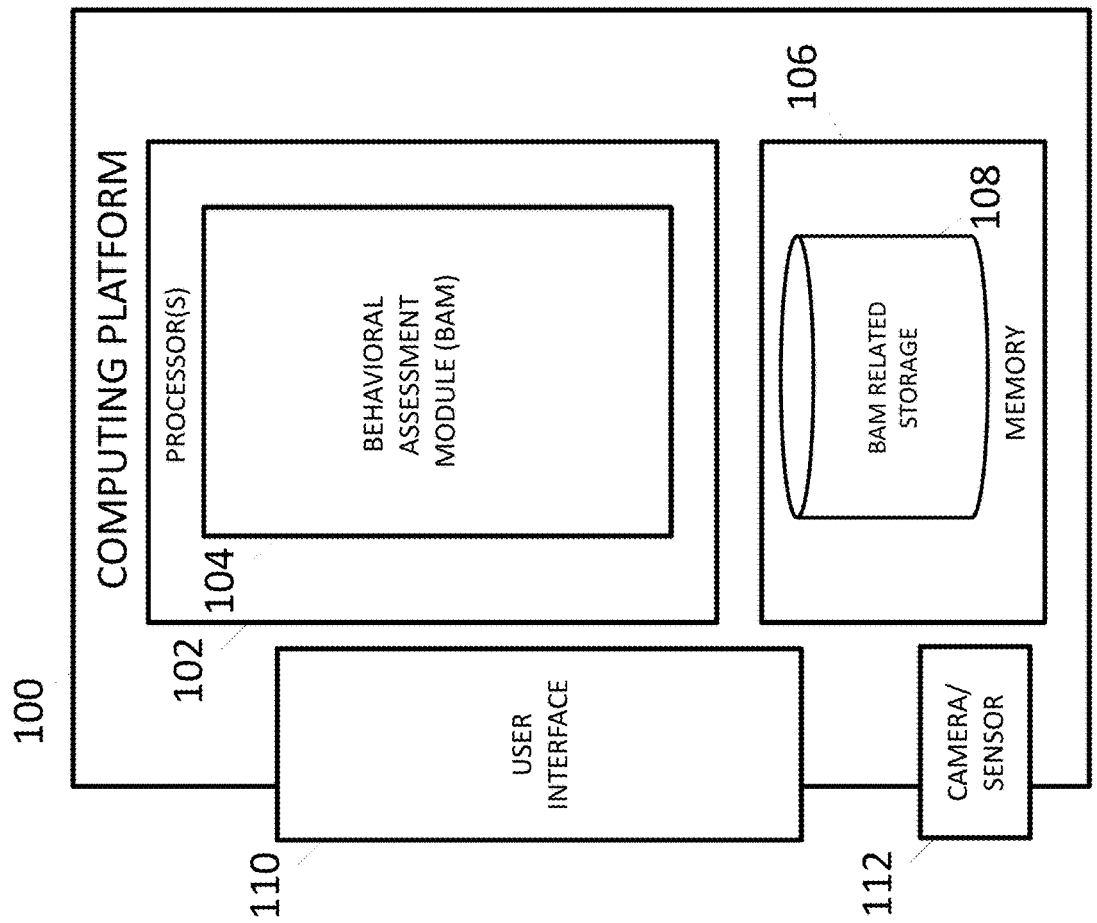
FIG. 1 is a diagram illustrating an exemplary computing platform for automated behavioral assessment according to an embodiment of the subject matter described herein

FIG. 1 is a diagram illustrating an exemplary computing platform 100 for automated behavioral assessment according to an embodiment of the subject matter described herein. Computing platform 100 may be any suitable entity (e.g., a mobile device or a server) configurable for performing automated behavioral assessments via monitoring (e.g., video and/or audio recording) users for responses to one or more stimuli and automatically analyzing or coding the responses for determining a behavioral assessment. For example, computer platform 100 may include a memory and a processor for executing a module (e.g., an app or other software) for automated behavioral assessment. In this example, computer platform 100 may also include a user interface for providing stimuli (e.g., video, audio and/or text) designed to illicit certain responses from a user (e.g., a child or toddler) and a camera for recording or obtaining responses to the provided stimuli. Continuing with this example, the app executing at computing platform 100 may use the recorded responses for coding and/or determining a behavior assessment (e.g., a diagnosis of a behavioral disorder or a related metric, such as a number between 0 and 10 indicating the likelihood of a user having a particular behavioral disorder).

Computing platform 100 may include processor(s) 102. Processor(s) 102 may represent any suitable entity or entities (e.g., hardware-based processor) for processing information and executing instructions or operations. Processor 102 may be any type of processor, such as a central processor unit (CPU), a microprocessor, a multi-core processor, and the like. Computing platform 100 may further include a memory 106 for storing information and instructions to be executed by processor 102.

In some embodiments, memory 106 can comprise one or more of random access memory (RAM), read only memory (ROM), static storage such as a magnetic or optical disk, or any other type of machine or non-transitory computer-readable medium. Computing platform 100 may further include a communication device (not shown), such as a network interface card or other communications interface, configured to provide communications access to various entities (e.g., other computing platforms). In some embodiments, memory 106 may be utilized to store a behavioral assessment module (BAM) 104, or software therein, and a BAM related storage 108.

BAM 104 may be any suitable entity (e.g., software executing on one or more processors) for performing one or more aspects associated with automated behavioral assessment. In some embodiments, BAM 104 may be configured to provide at least one stimulus for eliciting a response from a user, to obtain, using a camera communicatively coupled to the computing platform, the at least one response, and/or to determine, using the at least one response, a behavioral assessment associated with the user.

In some embodiments, BAM 104 and/or another module may generate, determine, and/or utilize stimuli (e.g., text, instructions, video, audio, etc.) for eliciting specific responses from a user. For example, BAM 104 and/or another module may instruct a user or a participant (e.g., the user's parent) to perform a task, e.g., to roll a ball, to speak a user's name at a particular time during the behavior assessment, or to stack a set of rings, where the instructed activity is intended to elicit a particular response (e.g., an emotion, a particular facial expression, a particular eye movement, or other response) from the user.

In some embodiments, BAM 104 may generate and/or utilize stimuli designed to exhibit various behaviors that are known or believed to be indicative of autism or other behavioral disorders. For example, the following symptoms have been shown to reliably detect risk for autism based on both retrospective and prospective (high risk infants) studies: overall sustained attention to complex stimuli, reduced range of affective expression (e.g., less smiling and/or more neutral responses), failure to orient to when a user's name is called, and lack of social referencing (e.g., turning head toward a parent to share interest in a surprising or engaging event). In this example, BAM 104 may generate and/or utilize stimuli such that a user's actions can be analyzed with regard to whether any of these symptoms were expressed.

Table 1 below indicates various potential stimuli that may be stored, generated, and/or used by BAM 104. As shown in Table 1, each stimulus may be associated with one or more constructs (e.g., certain traits, behaviors, or abilities) to be measured and one or more dependent variables that may affect how user responses are scored or interpreted. In some embodiments, BAM 104 may utilize one or more dependent variables when analyzing user responses (e.g., recordings of user) and may also be used to code and/or score user responses into quantitative metrics.

TABLE 1

| Stimuli | Construct measured | Dependent variable |
| --- | --- | --- |
| Bubbles with soft music (shown at beginning and end) | Baseline attentional engagement, social referencing, and range and intensity of affective expressions | # seconds attending to screen<br># full head turns to reference parent located behind child and whether temporally preceded by a smile<br>#, duration and intensity of specific facial expressions |
| Side-by-side presentation of a series of women singing nursery rhymes while making hand gestures on one side and a series of noise-making toys on other | Visual attention to social vs. nonsocial stimuli, social referencing, range and intensity of affective expressions | # seconds attending to social vs nonsocial stimuli<br># full head turns to reference parent located behind child and whether temporally preceded by a smile<br>#, duration, and intensity of specific facial expressions |
| Puppet show 1 - series of surprising and engaging events, including motorized bunny similar to that used in ADOS testing to elicit social referencing | Attentional engagement, social referencing, affective expressions | # seconds attending to screen<br># full head turns to reference parent located behind child whether temporally preceded by a smile<br>#, duration, and intensity of specific facial expressions |
| Child's name called by examiner (Right side, Left side) Sound emitted from toy held by adult (Right side, Left side) | Orient to social vs. nonsocial auditory stimuli | # and latency of head turns to right or left to examiner directly adjacent to child in response to name call vs. sound from toy activated by examiner |
| Puppet show 2 - displays a social conflict scene | Attentional engagement, social referencing, affective expressions | # seconds attending to screen<br># full head turns to reference parent located behind child and whether temporally preceded by a smile<br>#, duration, and intensity of specific facial expressions |
| Video of two young children arguing over a toy | Attentional engagement, social referencing, affective expressions | # seconds attending to screen<br># full head turns to reference parent located behind child and whether temporally preceded by a smile<br>#, duration, and intensity of specific facial expressions |
| Mirror reflects back child's spontaneous actions) | Attentional engagement, social referencing, affective expressions | # seconds attending to screen<br># full head turns to reference parent located behind child and whether temporally preceded by a smile<br>#, duration, and intensity of facial expressions |

In some embodiments, BAM 104 and/or another entity may store multiple video and/or audio clips, where each video and/or audio clip is designed for eliciting a particular response. In this example, BAM 104 and/or another module may determine, using one or more factors, a set of video and/or audio clips from the stored video and/or audio clips to use (e.g., provide or display to a user) for performing a behavioral assessment. Continuing with this example, factors that may determine which video and/or audio clips get used can include a user's age, a user's skills or knowledge (e.g., reading ability, number knowledge, alphabet knowledge, colors knowledge, shapes knowledge, etc.), medical history, risk factors (e.g., if a sibling has a particular behavioral disorder, if user was born premature, etc.), a user or other entity's preferences (e.g., a request to check for autism or ADHD), progress or treatment session information (e.g., if a user is receiving treatment for a given behavioral disorder, certain videos segments may be displayed each time to measure progress or different video segments may be used to avoid "cheating" or inaccurate results), whether or not a caregiver has been implementing suggestions made for alleviating previously reported symptoms, and/or other factors.

In some embodiments, stimuli may be modified or adapted to a user preference (e.g., preferred movies), a user's age, application task (e.g., autism screening, anxiety screening, etc.), ethnicity, socio-cultural background, or any other characteristic that is useful in performing behavioral assessment, e.g., helpful in studying and/or coding (e.g., identifying and/or scoring) behaviors in recorded user responses that are indicative of a behavioral disorder or normal behavior.

In some embodiments, BAM 104 may include or provide an app that performs automated behavioral coding and/or behavior assessment by interacting with a user and determining, based on the interactions, various stimuli to provide to the user for gathering additional information for the behavioral assessment. For example, BAM 104 and/or a related app may provide a user interface for providing questions (e.g., from a validated questionnaire, such as Modified Checklist for Autism in Toddlers (M-CHAT)) and receiving answers from a user or a user's caregiver. In this example, BAM 104 and/or a related app may determine one or more stimuli to provide to a user based on the questions. Continuing with this example, additional and/or dynamic stimuli may be provided to the user based on the user responses to prior stimuli. By using a dynamic and/or adaptive assessment model (e.g., where stimuli and/or the behavioral assessment is based at least in part on user feedback), BAM 104 and/or a related app can gather relevant behavior related information efficiently for performing tailored and/or personalized behavioral assessments.

In some embodiments, BAM 104 may utilize game mechanics (e.g., virtual rewards, points, additional minutes of entertainment, and/or other incentives) and/or other techniques for eliciting user responses or gathering information. For example, each video segment may include a particular interactive element that depending on the user's response may affect a subsequent video segment or other stimulus. In this example, the stimuli and user responses may act as a stimuli-feedback loop, where different or additional stimuli is determined based on one or more prior user responses.

In some embodiments, computing platform 100 and/or BAM 104 may be communicatively coupled to a user interface 110 and a camera and/or a sensor (camera/sensor) 112. User interface 110 may be any interface for providing information (e.g., output) to a user and/or for receiving information (e.g., input) from a user. In some embodiments, user interface 110 may include a graphical user interface (GUI) for providing a questionnaire and/or for receiving input from a user and/or a display screen for displaying various stimuli to a user.

Camera/sensor 112 may represent any suitable entity (e.g., a camera sensor or camera chip in a smartphone) for recording visual images, audio, and/or other user input (e.g., motion). For example, camera/sensor 112 may include a two dimensional camera, a three dimensional camera, a heat-sensor camera, a motion sensor, a gyroscope sensor, or any combination thereof. In some embodiments, camera/sensor 112 may be usable for recording a user during a behavioral assessment.

In some embodiments, camera/sensor 112 and/or BAM 104 may include functionality for identifying user responses. For example, camera/sensor 112 may be a three dimensional camera, such as a low-cost, three dimensional camera, configured to identify facial expressions or other responses associated with a moving or active subject (e.g., a face of a hyperactive young child). In this example, camera/sensor 112 and/or BAM 104 may include or utilize one or more algorithms for identifying a facial area using known or identifiable facial regions or landmarks (e.g., a nose, eyebrows, eyes, mouth, etc.) at various angles and/or head positions. Continuing with this example, camera/sensor 112 and/or BAM 104 may also include or utilize one or more algorithms for determining changes to the identified facial area and for determining whether such changes are indicative of one or more particular facial expressions or other responses. Representative algorithms are disclosed herein below.

In some embodiments, BAM 104 may include functionality for determining and monitoring a user's emotional expressiveness. For example, BAM 104 may track the number of emotions or facial expressions expressed by a user during a stimuli or test session. In this example, BAM 104 may analyze and/or use this information for determining whether a user is exhibiting symptoms of one or more behavioral disorders.

In some embodiments, BAM 104 may include functionality for analyzing video of a user for determining whether one or more responses are indicative of a behavioral disorder. For example, during an automated behavioral assessment, BAM 104 may analyze video of a user for responses to one or more provided stimuli. In this example, BAM 104 may compare the user responses and predetermined base (e.g., "normal" or appropriate) responses for determining whether the user responses are indicative of a behavioral disorder.

In some embodiments, analyzing videos and/or other responses may include behavioral coding. Behavioral coding may include identifying and/or scoring user responses into quantitative metrics and may be automated (e.g., performed without user (e.g., human) assistance). For example, coding may involve one or more algorithms or techniques for identifying (e.g., from a recording of a user) various user responses (e.g., "smiling", "turning head", "crying", etc.). In this example, coding may also include one or more algorithms or techniques for scoring identified user responses, e.g., into quantitative metrics that can be compared and/or processed. In another example, behavioral analysis and/or coding may include detecting a user's failure to disengage their attention (e.g., in response to having their name called) and/or to socially reference (e.g., by turning their head to) a parent in response to surprising or engaging stimuli. In yet another example, behavioral analysis and/or coding may include detecting a user's lack of emotional expressiveness and/or fewer smiles (e.g., happy expressions) as compared to a baseline.

In some embodiments, BAM 104 may use one or more algorithms and/or techniques for combining, normalizing, weighting, and/or utilizing metrics associated with one or more modalities (e.g., questionnaires, recordings of user, medical history, clinical studies, etc.) in performing automated behavioral assessments. For example, BAM 104 may utilize a behavioral assessment algorithm that receives metrics associated with a questionnaire and metrics associated with recorded user responses. In this example, the behavioral assessment algorithm may normalize each set of metrics, e.g., adjusting each set of metrics to fit a same range or scoring scale. Continuing with this example, the behavioral assessment algorithm may weight each set of metrics based on one or more factors, e.g., questionnaire metrics may be weighted at 60% and response metrics may be weighted at 40% when combining or aggregating the sets of metrics to derive a total or aggregate score associated with a behavioral assessment.

In some embodiments, BAM 104 may use received user information along with predetermined information (e.g., scientifically recommended or clinically-approved information associated with diagnosing behavioral disorders or for coding responses to particular behavioral disorders) for automated behavioral assessment. For example, questions for determining risk factors and/or other information may be presented to a user or a caregiver, where the questions are based on clinically-approved questions for identifying a behavioral disorder. In another example, stimuli and base responses (e.g., "normal" responses used for comparisons to user responses) may be generated using information about the user along with predetermined information associated with numerous clinical research or medical studies.

In some embodiments, BAM 104 may include functionality for tracking progress of a user. For example, depending on an initial behavioral assessment, BAM 104 may be configured to perform subsequent coding and assessments after the initial assessment and to track progress associated with the various assessments. In this example, tracking progress may also include providing dynamic recommendations or various strategies to the user or caregiver for improving or alleviating symptoms of the behavioral disorder.

In some embodiments, BAM 104 may include functionality for aggregating behavioral related information associated with one or more users and/or assessment sessions. In such embodiments, the aggregated behavioral related information may be usable for behavioral assessments, cost/benefit analysis, improving therapies and/or treatments, and/or other purposes. For example, BAM 104 may be configured to track progress of one or more users associated with a given treatment or therapy (e.g., intervention). In this example, the progress of the one or more users for the given treatment or therapy may be processed to generate aggregate metrics and/or may be usable in performing a cost-benefit analysis for the given treatment. In another example, aggregate metrics and/or data associated with multiple users may be utilized in adjusting or modifying various algorithms and/or techniques associated with performing automated behavioral assessment, e.g., including behavioral analysis and/or coding.

In some embodiments, BAM 104 may determine and/or provide a behavioral assessment and/or related information (e.g., follow-up information and/or progress information) to one or more entities, such as a user, a medical records system, a healthcare provider, a caregiver of the user, or any combination thereof. For example, a behavioral assessment and/or related information may be provided via a phone call, a social networking message (e.g., Facebook or Twitter), an email, or a text message. In another example, a behavioral assessment may be provided via an app and/or user interface 110. When provided via an app, the behavioral assessment may include progress information associated with a user. For example, progress information associated with a user may indicate (e.g., to a caregiver or physician) whether certain therapies and/or strategies are improving or alleviating symptoms associated with a particular behavior disorder. In another example, progress information may include aggregated information associated with multiple stimuli and/or assessment sessions.

In some embodiments, follow-up information may be provided to a user for communicating with a service provider. For example, a user may be provided a FaceTime® identifier for video chatting with a physician or healthcare worker remotely. In another example, a user may be provided with a list of relevant specialists in a geographical area near the user.

In some embodiments, BAM 104 may include functionality for allowing a user or other entity control or limit dissemination of information that is collected, obtained, or analyzed. In some embodiments, BAM 104 may provide privacy protocols and/or security mechanisms that are Health Insurance Portability and Accountability Act (HIPAA) compliant. In some embodiments, BAM 104 may provide configurable privacy settings via user interface 110 that prevent recordings of a user from being viewed by or sent to unauthorized entities (e.g., health insurance companies) and/or may indicate which, if any, entities may receive behavioral assessments or related information therein.

Memory 106 may be any suitable entity (e.g., a non-transitory computer readable medium) for storing information. Memory 106 may include a BAM related storage 108. BAM related storage 108 may be any suitable entity (e.g., a database embodied or stored in computer readable media) storing user data, stimuli, recorded responses, and/or predetermined information. For example, BAM related storage 108 may include user data, such as age, name, knowledge, skills, sex, and/or medical history. BAM related storage 108 may also include predetermined information, including information gathered by clinical studies, patient and/or caregiver surveys, and/or doctor assessments. The predetermined information may include information for analyzing responses, information for determining based responses, information for determining assessment thresholds, coping strategies, recommendations (e.g., for a caregiver or a child), treatment and/or related therapies, information for generating stimuli and/or selecting appropriate stimuli for an automated behavioral assessment, and/or other information. In some embodiments, BAM related storage 108 or another entity may maintain associations between relevant health information and a given user or a given population (e.g., users with similar characteristics and/or within a similar geographical location). For example, users associated with different conditions and/or age groups may be associated with different recommendations, base responses, and/or assessment thresholds for indicating whether user responses are indicative of behavioral disorders.

In some embodiments, BAM related storage 108 may be accessible by BAM 104 and/or other modules of computing platform 100 and may be located externally to or integrated with BAM 104 and/or computing platform 100. For example, BAM related storage 108 may be stored at a server located remotely from a mobile device containing BAM 104 but still accessible by BAM 104. In another example, BAM related storage 108 may be located at distributed or separated across multiple nodes.

It will be appreciated that the above described modules are for illustrative purposes and that features or portions of features described herein may be performed by different and/or additional modules, components, or nodes. For example, aspects of automated behavioral assessment described herein may be performed by BAM 104, computing platform 100, and/or other modules or nodes.

Figure 2:
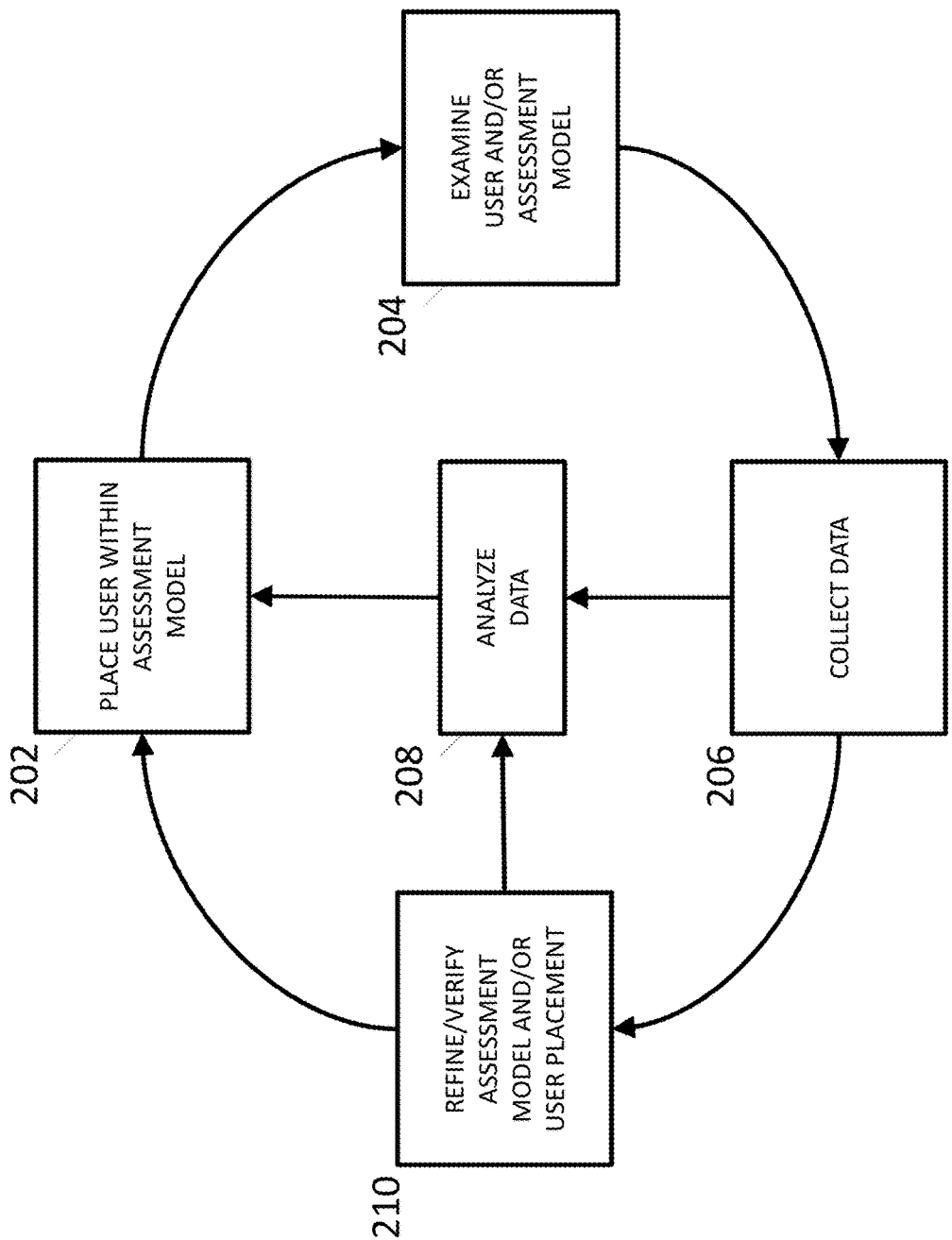
FIG. 2 is a diagram illustrating an adaptive assessment model according to an embodiment of the subject matter described herein.

FIG. 2 is a diagram illustrating an adaptive assessment model 200 according to an embodiment of the subject matter described herein. In some embodiments, adaptive assessment model 200 may be usable by BAM 104 and/or a related app and may represent a stimuli-feedback loop. For example, adaptive assessment model 200 may represent various steps for generating and/or providing relevant stimuli for efficiently performing automated behavioral assessment, e.g., by determining, based on received input, whether or not additional input is needed to complete a behavioral assessment. In this example, if additional input is needed, adaptive assessment model 200 may determine what stimuli should be provided to elicit the necessary input from the user.

In some embodiments, adaptive assessment model 200 may include steps 202-210. In step 202, a user is placed within adaptive assessment model 200. For example, using known information about a user or a related user population, BAM 104, using adaptive assessment model 200, may indicate a particular set of questions, videos, and/or other stimuli to prove to the user for eliciting user responses. In this example, some users may be presented different questions, videos, and/or other stimuli than other users, e.g., depending on a particular goal of a caregiver, such as an autism screening or an anxiety screening.

In step 204, a user and/or adaptive assessment model 200 may be examined. For example, BAM 104, using adaptive assessment model 200, may provide stimuli to a user, e.g., via communications interface 110 and/or camera/sensor 112.

In step 206, data may be collected. For example, BAM 104, using adaptive assessment model 200, may record or otherwise monitor user responses to provided stimuli.

In step 208, collected data may be analyzed. For example, BAM 104, using adaptive assessment model 200, may analyze (e.g., code) user responses and/or perform a behavioral assessment associated with the collected data. In another example, other information, such as aggregated behavioral related information associated with multiple users, may be analyzed for modifying and/or changing various aspects of adaptive assessment model 200, including user placement, stimuli selection, and/or behavioral assessment or analysis.

In step 210, adaptive assessment model 200 and/or user placement (e.g., step 202) may be refined and/or verified. For example, BAM 104, using adaptive assessment model 200, may determine whether a user is properly assessed by using feedback associated from the user, an independent observer, and/or similar users. In this example, using collected information and/or related analysis, BAM 104, using adaptive assessment model 200, may refine, adapt, and/or change user placement and/or stimuli selection for subsequent assessment sessions and/or subsequent users. In another example, BAM 104, using adaptive assessment model 200, may examine various algorithms and/or techniques for deriving an automated behavior assessment and, using collected information and/or related analysis, may refine, adapt, and/or change algorithms, techniques, and/or other factors that affect behavioral assessment.

It will be appreciated that adaptive assessment model 200 is for illustrative purposes and that different and/or additional actions may be used. It will also be appreciated that various actions described herein may occur in a different order or sequence.

Figure 3:
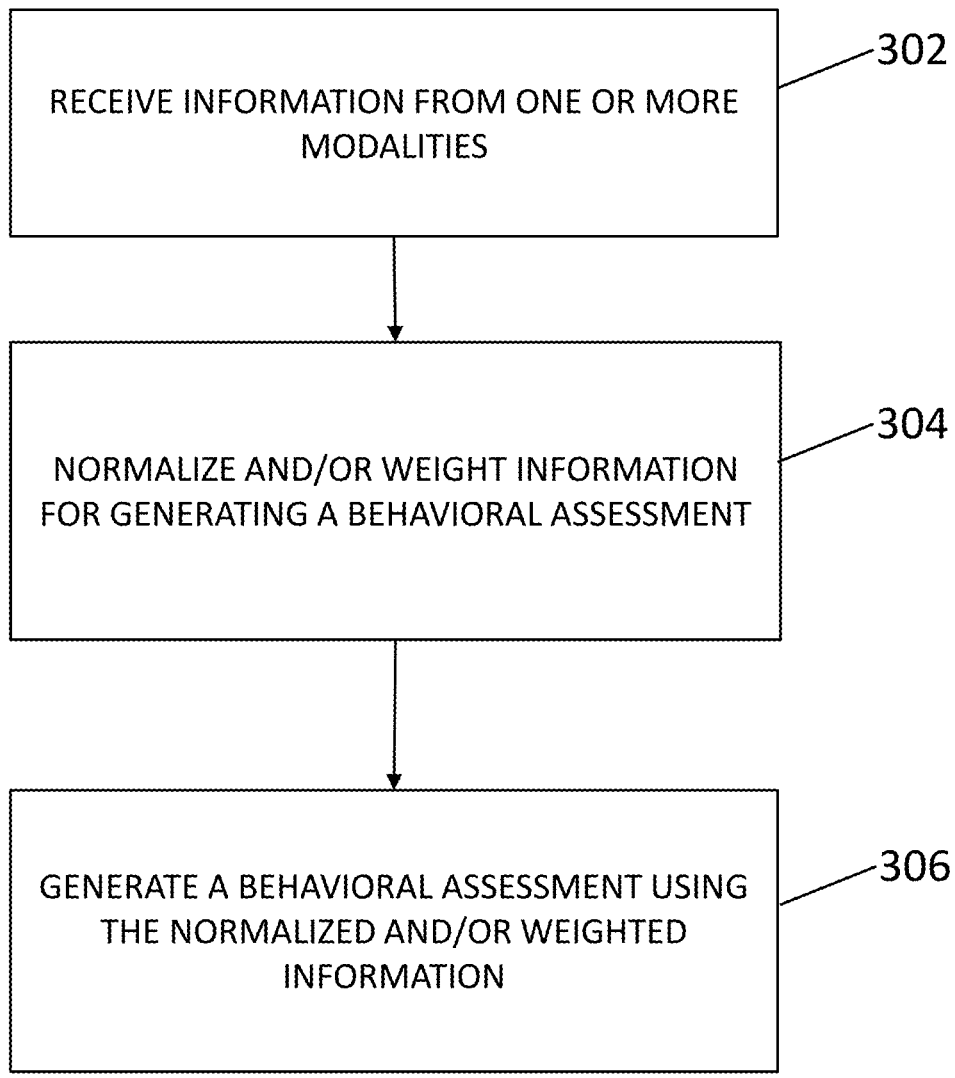
FIG. 3 is a diagram illustrating a behavioral assessment algorithm according to an embodiment of the subject matter described herein.

FIG. 3 is a diagram illustrating a behavioral assessment algorithm 300 according to an embodiment of the subject matter described herein. In some embodiments, behavioral assessment algorithm 300 may be usable by BAM 104 and/or a related app for generating a behavioral assessment using information associated with one or more modalities (e.g., questionnaires, video recordings, and/or other feedback mechanisms).

In some embodiments, behavioral assessment algorithm 300 may include steps 302-306. In step 302, information from one or more modalities is received. For example, received information may include raw data and/or scored data (e.g., metrics associated with a scale or score related to a corresponding modality). For example, each answer to a question in a questionnaire may be scored using an integer between 0 and 5. In this example, behavioral assessment algorithm 300 may receive each scored answer value along with the actual answer and/or corresponding question. In another example, recorded user responses may be analyzed and scored based on dependent variables, where scoring may involve using an integer between 0 and 10. In this example, behavioral assessment algorithm 300 may receive stimuli provided, the recorded user responses, and scored dependent variables, and the related scores.

In step 304, the received information may be normalized, weighted, and/or processed for generating a behavioral assessment. For example, behavioral assessment algorithm 300 may adjust one or more sets of metrics having different scoring scales so that the sets of metrics use a common scoring scale. In this example, assuming that a set of answers to a questionnaire is associated with a 0-5 scoring scale and assuming a set of user responses is associated with a 0-10 scoring scale, behavioral assessment algorithm 300 may double answer values such that each answer value is between 0-10.

In some embodiments, information associated with different modalities may be weighted or otherwise modified such that some information is given more weight or influence in affecting or determining a behavioral assessment than other information. For example, behavioral assessment algorithm 300 may generate an aggregate behavioral assessment score, where 60% of the score is based on answers to a questionnaire and 40% of the score is based on recorded user responses.

In step 306, a behavior assessment may be generated using the normalized and/or weighted information. For example, behavioral assessment algorithm 300 may generate a behavioral assessment using an aggregate assessment score. In this example, the aggregated assessment score may be an integer between 0 and 100, where any score under 80 indicates a low probability of a user having a behavioral disorder or related symptoms and where any score over 80 indicates at least a moderate probability of a user having a behavioral disorder or related symptoms.

It will be appreciated that behavioral assessment algorithm 300 is for illustrative purposes and that different and/or additional actions may be used for performing an automated behavioral assessment. It will also be appreciated that various actions described herein may occur in a different order or sequence.

Figure 4A:
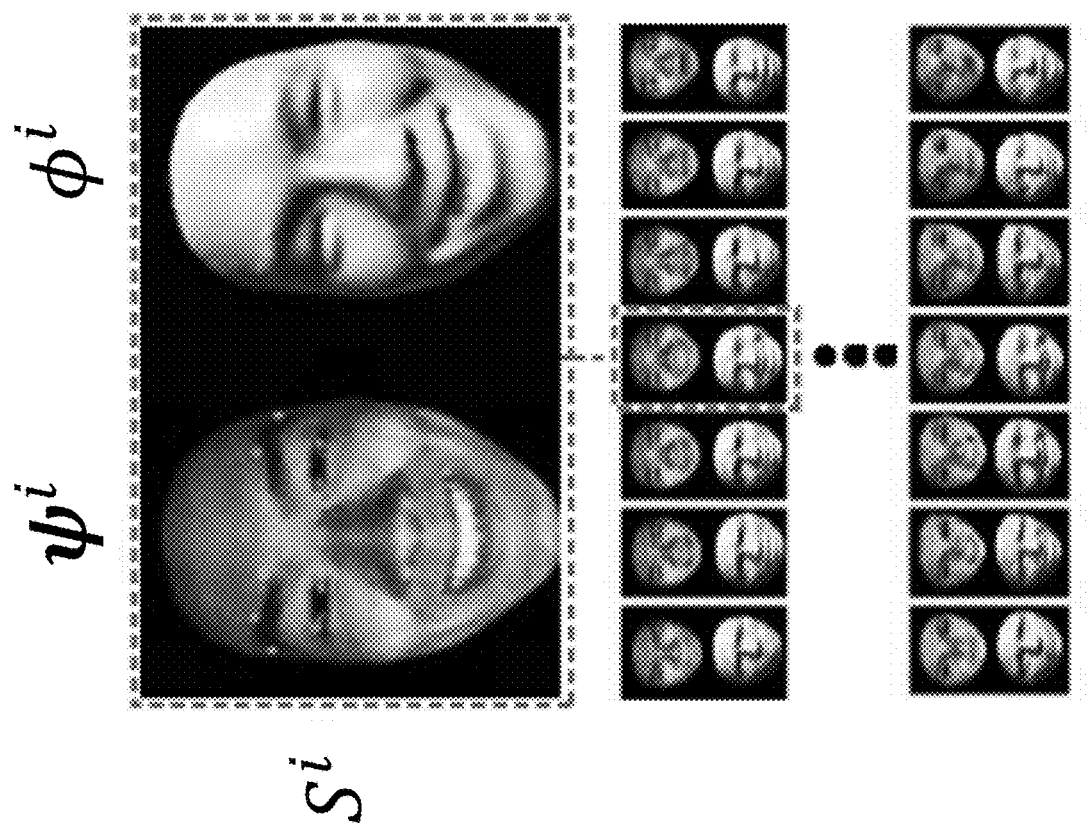
FIGS. 4A-4D are diagrams illustrating aspects of example techniques for identifying facial expressions according to an embodiment of the subject matter described herein.
Figure 4B:
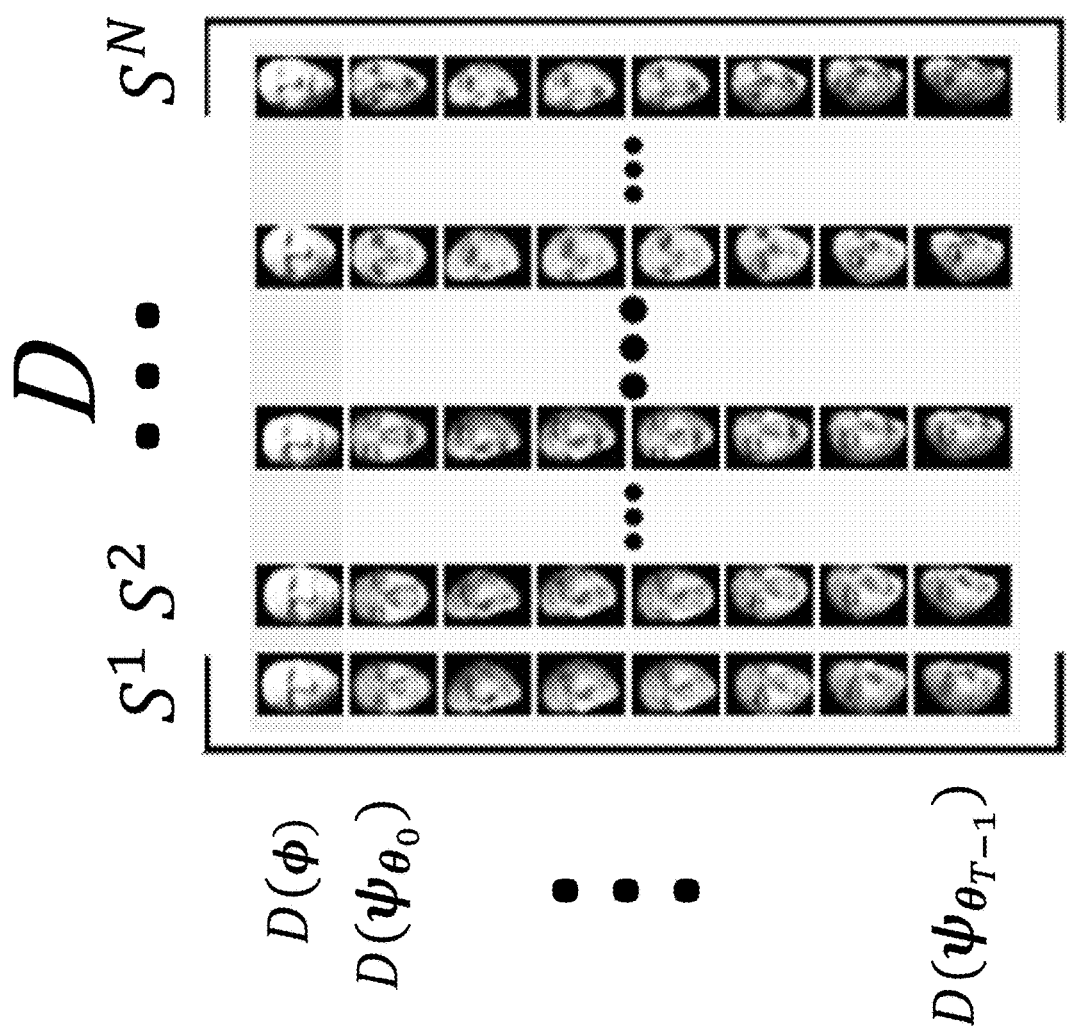

FIGS. 4A-4D are diagrams illustrating aspects of example techniques for identifying facial expressions according to an embodiment of the subject matter described herein. FIG. 4A depicts samples of 3D textured face scans from the BU3D-FE dataset (a multi-view 3D facial expression recognition dataset provided by Binghamton University), where each sample $S^i$ can be decomposed into a 3D and a 2D component, $\psi^i$ and $\phi^i$ respectively. The used 19 facial landmarks are highlighted with gray markers. FIG. 4B depicts a dictionary composed of blocks containing different modalities and poses. The highlighted section represents dictionary block $D(\phi)$ containing 3D features, while the other sections represent dictionary blocks $D(\psi_{\theta_j})$ containing 2D features from the synthesized head poses $\theta_j$.

Figure 4C:
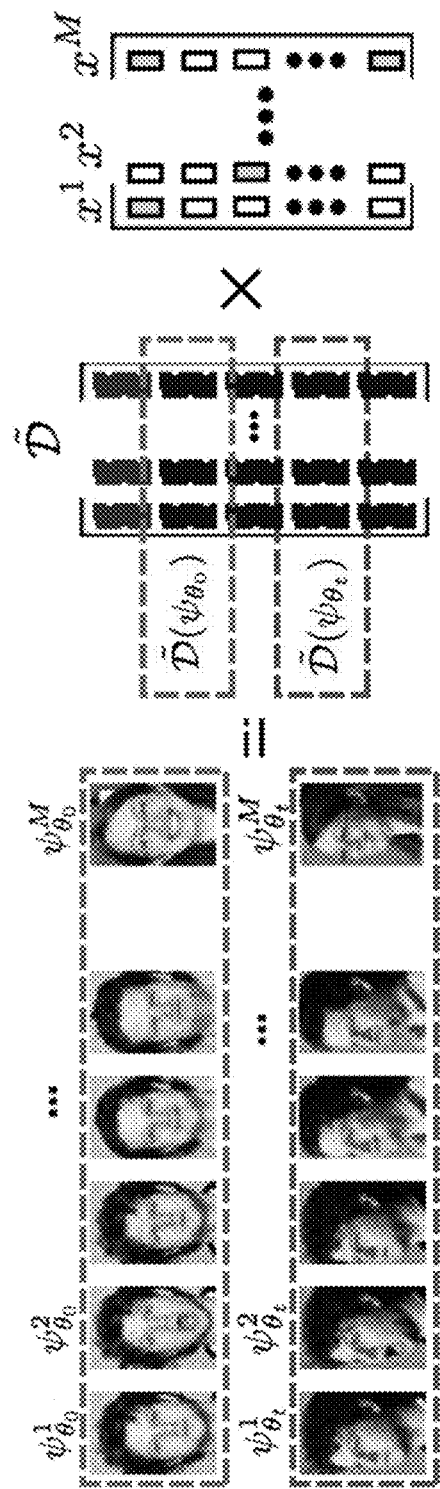
Figure 4D:
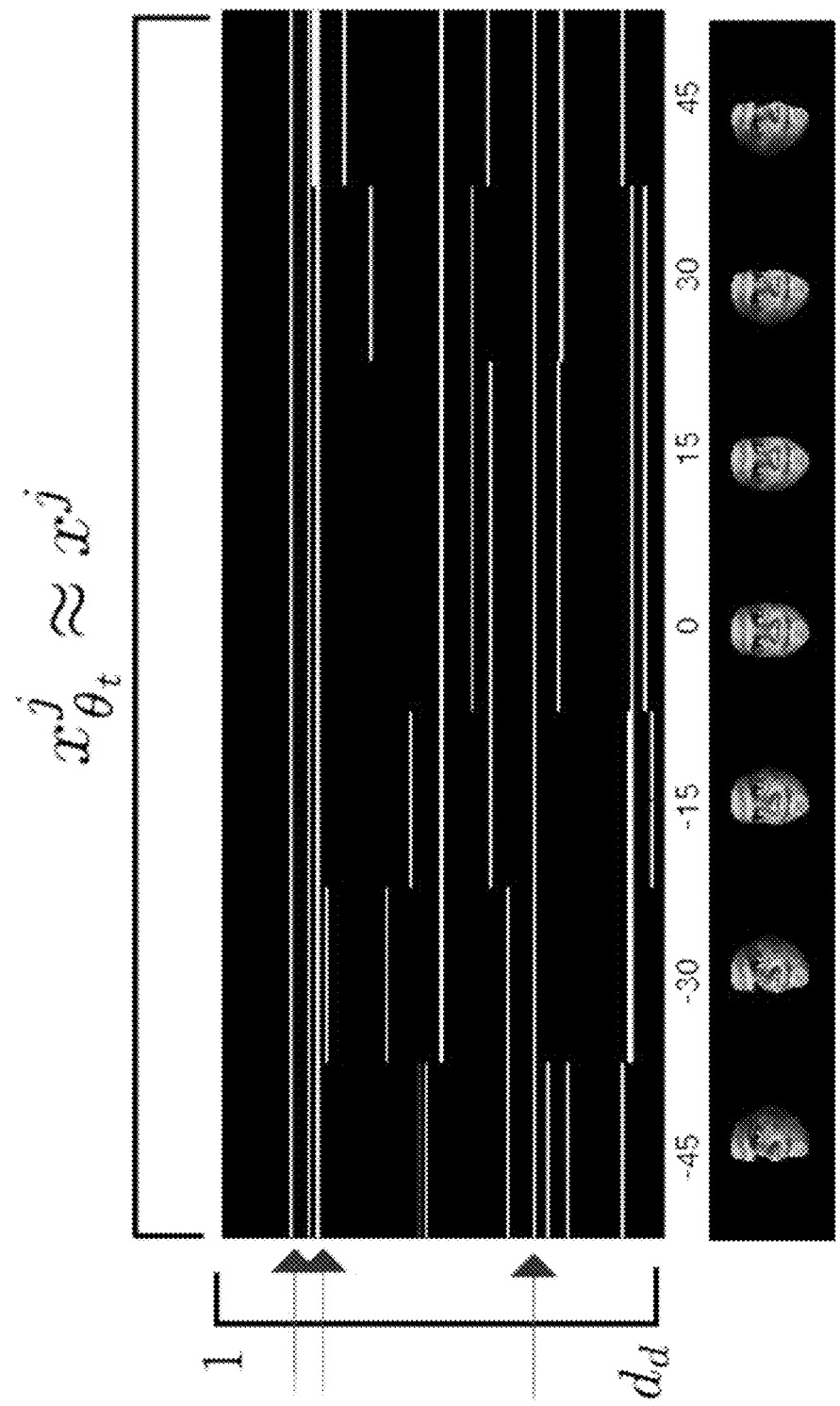

FIG. 4C depicts an overview of a cross-modality and pose-invariant representation and examples from the MultiPie dataset (a dataset of faces collected by Carnegie Mellon University). As depicted in FIG. 4C, given the dictionary $\tilde{D}$, it is proposed that the sparse coefficient vectors between the same subjects performing the same expressions at different poses or modalities will be nearly identical. The dotted boxes around the faces (top and bottom) represent observation of the same subjects from a given expression at different poses. These observations can be represented by a linear combination of the same sparse coefficients being applied to a given sub-dictionary of $\tilde{D}$, that is represented with the respective dotted boxes. FIG. 4D depicts an example of the sparse coefficient vectors extracted from a subject performing a disgust expression at 7 poses. Each of the 7 columns in the image correspond to a sparse coefficient vector $X^j$ extracted at a given pose, and the rows represent weights corresponding to atoms in $\tilde{D}$. Images of the input subject are shown below each pose. Notice the horizontal line structure (depicted by the arrows) throughout the sparse coefficient vectors at different poses, reinforcing the notation that the sparse coefficients extracted for different poses are approximately consistent thus pose invariant.

The analysis of facial expression is studied in computer vision, psychology, psychiatry, and marketing, all of which require a facial expression recognition (FER) system to be robust to changes in pose. In particular for the psychology and psychiatry fields, risk signs of anxiety and autism can be depicted from facial expressions as the participant is looking at various stimuli [1, 2]. Robustness to pose is especially important since the experts need to analyze participants in their natural states, in other words being observed in an unconstrained manner (see [3] and [4] for examples). Many state of the art facial expression approaches focus on frontal or nearly frontal images of the face [5, 6]. Changes in head pose or facial expression cause nonlinear transformations of the face in a 2D image, making it a non-trivial task to classify expressions under varying poses [7]. Even with recent FER advancements, manually coding of facial expression is still performed in the psychiatry and psychology fields due in part to this challenge.

Approaches to handle facial expression across multiple poses fall within two main categories. The first category corresponds to approaches based on learning expression models on a discrete set of poses [8, 9]. For example, [8] employ a 2 stage approach where they first train a classifier to distinguish pose, and then train pose-dependent classifiers across expressions. The second category involves approaches that learn the mappings of the expressions as a function of pose [10, 11, 12]. Notably, [10] presents an accurate geometric based approach to first learn the transformation of facial points at any given pose to a frontal pose, then FER is performed on facial points from the projected frontal pose, thus requiring only one posed classifier. The work [12] adopts a Partial Least Squares approach, that has been explored in facial recognition, to model the relations between pairs of images of the same person at different poses and expressions.

In addition to FER in 2D images, much attention has been focused on using 3D face scans [13, 14]. Specifically, textured 3D face scans not only contain 3D features (e.g., morphological and shape), but also 2D features (e.g., geometric and texture). Zhao et al. [13] have shown that when dealing with 2D and 3D features independently on a frontal face, the ordering of discriminative power for FER is morphological, shape, and texture; and combining all three feature modalities together achieves the strongest discriminative power. Although textured 3D face scans provide the most discriminative features, technology has not yet allowed for practical acquisition in unconstrained environments, such as capturing child facial behaviors in a doctor's office.

Dictionary based approaches have been extensively used for classification and regression in the areas of facial recognition and expression [15, 16]. Furthermore, sparse based methods can be applied by incorporating regularized penalty functions to determine sparse coefficients in a more greedy fashion [16, 17]. By encoding structure along atoms in the dictionary, such as annotating or grouping atoms in the dictionary with class labels, the sparse coefficients can provide knowledge to the class that the unseen face belongs to. Recent work has also focused on encoding structure within the atoms themselves, namely domain adaptive dictionary learning [18].

In some embodiments, BAM 104 or behavioral assessment algorithm 300 may utilize a robust, cross-modality, and/or pose-invariant dictionary for recognizing facial expressions. For example, BAM 104 may use a framework that first learns a dictionary that i) contains both 3D shape and morphological information as well as 2D texture and geometric information, ii) enforces coherence across both 2D and 3D modalities and different poses, and iii) is robust in the sense that a learned dictionary can be applied to multiple facial expression datasets. Using the dictionary based approach, significant results in the task of pose-invariant FER can be achieved.

In some embodiments, an example technique for identifying a facial expression and/or determining a behavioral assessment may include constructing a cross-modality and/or pose-invariant dictionary and applying it to the task of pose-invariant FER. FIGS. 4A-4D depicts the outline of this approach for dictionary construction and cross domain representation.

In some embodiments, BAM 104 or behavioral assessment algorithm 300 may utilize an example pose-invariant dictionary as below. Given a dataset containing N textured 3D face scans under varying expressions, each sample may be defined as $S^i = \{\phi^i, \psi^i\}$, where $i=1, 2, \ldots, N$, and $\phi^i$ and $\psi^i$ represent the 3D specific and 2D specific information from sample i, respectively. From a single textured 3D face scan, 2D images with varying head poses, $\theta$, can be synthesized. In this sense, a sample can be decomposed as $$S^i = \{\phi^i, \psi^i_{\theta_t}{}_{t=0}^{T-1}\},$$

with T different head poses, $\theta_0$ represents a frontal face, and $\psi^i_{\theta_t}$ represents 2D specific information at pose $\theta_t$ for sample i. Note that 3D specific information may not change with varying head poses. For all samples, the dictionary block $D(\phi) \in R^{d_m \times N}$ of extracted 3D features may be defined as $$D(\phi) = [f(\phi^1), f(\phi^2), \ldots, f(\phi^N)],$$

where $f(\phi^i) \in R^{d_m}$ represents the column array of computed frontal 3D features from the $i^{th}$ sample. Similarly, for all samples with simulated head pose $\theta_t$, the block $D(\psi_{\theta_t}) \in R^{d_n \times N}$ of extracted 2D features may be defined as $$D(\psi_{\theta_t}) = [f(\psi_{\theta_t}^1), f(\psi_{\theta_t}^2), \ldots, f(\psi_{\theta_t}^N)],$$

where $f(\psi_{\theta_t}^i) \in R^{d_n}$, represents the column array of computed 2D features from the $i^{th}$ sample at pose $\theta_t$.

The cross-modal and pose-invariant dictionary, D, may be organized by stacking the dictionary blocks (see FIGS. 4A-4B)

$$D = [D(\phi); D(\psi_{\theta_0}); D(\psi_{\theta_1}); \ldots; D(\psi_{\theta_{T-1}})],$$

with the stacking operator $$[D(\phi); D(\psi_{\theta_0})] = \begin{bmatrix} D(\phi) \\ D(\psi_{\theta_0}) \end{bmatrix}.$$

$D \in R^{(d_m + T \times d_n) \times N}$ is composed of a total of T+1 blocks, specifically one block containing the 3D features, $D(\phi)$, and T blocks containing the 2D features from each of the T simulated head poses, $$D(\psi^i_{\theta_t}{}_{t=0}^{T-1}).$$

This block structure within the dictionary D imposes coherence across the different domains.

By applying a dictionary learning method a more compact dictionary may be learnt, such as K-SVD [21], creating a new dictionary $\tilde{D} \in R^{(d_m + T \times d_n) \times d_d}$ where $d_d \leq N$. Note that since the block structure still remains, the coherence between the domains is preserved: D is transferred to $\tilde{D} = [\tilde{D}(\phi_{\theta_0}); \tilde{D}(\psi_{\theta_0}); \tilde{D}(\psi_{\theta_1}); \ldots; \tilde{D}(\psi_{\theta_{T-1}})]$, where now $\tilde{D}(\phi) \in R^{d_m \times d_d}$ and $\tilde{D}(\psi_{\theta_t}^i) \in R^{d_n \times d_d}$ (see FIGS. 4A-4B).

In some embodiments, the learned dictionary, $\tilde{D}$, contains a dense amount of expression information jointly learned across multiple domains (3 D and different poses in 2 D). Let unseen samples containing expression class labels and only 2D images at any pose $\theta_i$ be defined as $Q^j = \{\psi_{\theta_i}^j, L^j\}$, where j=1, 2, ..., M represent the samples and $L^j$=1, 2, ..., C represents the class label of the $j^{th}$ sample taking the values of C possible classes. The goal is to represent $Q^j$ as a sparse linear combination of the frontal 3D and frontal 2D features in $\tilde{D}$, namely $[\tilde{D}(\phi_{\theta_0}); D(\psi_{\theta_0})]$, since they are know to have large discrimination power for FER. Thus, the equation to solve is:

$$\{\tilde{Q}^j, x^j\} = \operatorname{argmin}_{x^j, Q^j} \|\tilde{Q}^j - [\tilde{D}(\phi); \tilde{D}(\psi_{\theta_0})]x^j\|_2^2$$

$$\text{s.t.} \|x^j\|_0 \le \lambda, \quad (1)$$

where $x^j \in R^{d_d}$ is the sparse coefficient vector, $\tilde{Q}^j \in R^{(d_n+d_m)}$ is the transformed version of sample $Q^j$ onto the domains represented by $[\tilde{D}(\phi); \tilde{D}(\psi_{\theta_0})]$, $\|x^j\|_0$ counts the number of non-zeros values in $x^j$, and $\lambda$ is the imposed sparsity constant. (1) is not directly solvable since the 3D information and frontal 2D information, $\tilde{Q}^j$, and the sparse coefficient vector, $x^j$, are unknown. Instead, the unknown 3D and frontal 2D information may be represented via the domain adaptive dictionary. It is proposed that the computed sparse coefficient vector in the known domain provided by $Q^j$ can be directly applied to dictionary blocks in unseen domains to estimate $\tilde{Q}^j$.

Since $Q^j$ provides information in the domain $\psi_{\theta_t}^j$, the sparse coefficient vector can be determined from:

$$x^j = \operatorname{argmin}_{x^j} \|\psi_{\theta_t}^j - \tilde{D}(\psi_{\theta_t})x^j\|_2^2, \text{s.t.} \|x^j\|_0 \le \lambda.$$

If $\theta_t$ is unknown, it can be estimated from a variety of head pose approaches [22] or by determining which domain block in $\tilde{D}$ gives the lowest reconstruction error. Due to the coherence across domains within the stacks of the dictionary $\tilde{D}$, it is assumed that the sparse coefficient vector, $x^j$, should not differ greatly between extracted data of the same subject but in different domains (see FIG. 4C). In other words, $$x^j = \operatorname{argmin}_{x^j} \|\psi_{\theta_t}^j - \tilde{D}(\psi_{\theta_t})x^j\|_2^2, \text{s.t.} \|x^j\|_0 \le \lambda \quad (2)$$

$$\approx \operatorname{argmin}_{x^j} \|\psi_{\theta_{t'} \ne t}^j - \tilde{D}(\psi_{\theta_{t'} \ne t})x^j\|_2^2, \text{s.t.} \|x^j\|_0 \le \lambda$$

$$\approx \operatorname{argmin}_{x^j} \|\phi^j - \tilde{D}(\phi)x^j\|_2^2, \text{s.t.} \|x^j\|_0 \le \lambda. \quad (3)$$

This assumption is explored and further validated below with regard to FIGS. 4C-4D. Equations (2) and (3) state that $x^j$ can be determined from any domain that lies in both $Q^j$ and $\tilde{D}$. Once $x^j$ is determined, $\tilde{Q}^j$ can be computed from (1).

To evaluate a proposed method described above, two publicly available face datasets were used: the BU3D-FE and the MultiPie datasets. The BU3D-FE dataset consists of textured 3D face scans of 100 subjects performing 6 different expressions: Anger (AN), Disgust (DI), Fear (FE), Happy (HA), Sad (SA), Surprised (SU) at 4 different levels, and a Neutral (NE) expression (see FIGS. 4A-4B for examples). For this demonstration, the data from the maximum level which corresponds to the apex of the expression was considered. From the MultiPie dataset, 2D images were selected from 160 subjects performing 4 different expressions: DI, HA, SU, and NE at 7 different yaw angles (0, -45, -30, -15, 15, 30, 45) (see FIG. 4C for examples). The MultiPie dataset also contains each expression and pose at different illuminations; however, the data from the frontal illumination is only considered.

To compute features from the datasets, 49 facial landmarks were automatically extracted with the IntraFace software [23]. Faces were aligned and normalized to a mean face across the BU3D-FE dataset using the inner-eye landmarks and the spine of nose. For selection of 2D and 3D features, we followed the state of the art approach in [13], where four modalities of features consisting of morphological, shape, texture, and geometric features are computed around 19 of the facial landmark points (see FIGS. 4A-4B). 3D morphological features consist of 157 Euclidean distance pairs between the 19 landmarks on the range data of the faces. 3D shape features consist of multi-scale local binary pattern (LBP) patches around each of the 19 landmarks on the image of the range data. Specifically, LBP with radii ranging from 1 to 5 were computed, where the total features extracted across all the patches at a given LBP scale is 4275. 2D texture features are computed in the same manner as the 3D shape features except extracted on the 2D textured images. 2D geometric features consist of the same distance pairs as the 3D morphological features, but the range value of each landmark is not considered. Principal component analysis (PCA) is performed on each modality independently, preserving at least 95% of the variation, thus reducing the dimensions of the morphological, shape, texture, and geometric features to 100, 1000, 1000, 100 respectively. Thus in the following experiments $d_n = d_m = 1100$. For all experiments shown, 2D images containing 7 poses with yaw angles (0, -45, -30, -15, 15, 30, 45) were considered.

The sparse coefficient vectors for the projected discriminant frontal $\tilde{Q}^j$ representations were determined through Orthogonal Matching Pursuit (OMP) with sparsity constant $$\lambda = \frac{1}{7} d_d,$$

since the dictionary is composed of an even representation of samples across 7 expressions. For each experiment, a single facial expression classifier was trained by applying to the extracted $\tilde{Q}^j$ representations a multi-class Support Vector Machine (SVM) [24] with a radial basis function kernel. Experiments described below perform a five-fold cross validation procedure to construct and test on the pose-invariant dictionary. Out of the samples chosen for constructing the dictionary, a ten-fold cross validation procedure was performed to determine the optimal SVM parameters.

TABLE 1

Comparisons of recognition rates (%) for varying expression (expr.) across different methods on BU3D-FE dataset, including a 3D specific framework [13], a pose-invariant framework [10], and our proposed approach when Neutral is and is not included. Note that [13] only considers a frontal pose and use 3D data for testing, while an approach described herein uses a more general and challenging testing setup.

| | Expr. | | | | | | | |
| --- | --- | --- | --- | --- | --- | --- | --- | --- |
| Appr. | AN | DI | FE | HA | SA | SU | NE | Total |
| 3D [13] | 83 | 87 | 68 | 93 | 83 | 95 | — | 85 |
| Proposed | 85 | 85 | 75 | 91 | 77 | 94 | — | 85 |
| 2D [10] | 68 | 75 | 63 | 81 | 63 | 82 | 71 | 77 |
| Proposed w/NE | 82 | 85 | 72 | 91 | 66 | 94 | 81 | 82 |

Table 1: Comparisons of recognition rates (%) for varying expression (expr.) across different methods on BU3D-FE dataset, including a 3D specific framework [13], a pose-invariant framework [10], and our proposed approach when Neutral is and is not included. Note that [13] only considers a frontal pose and use 3D data for testing, while an approach described herein uses a more general and challenging testing setup.

Experiments performed on the BU3D-FE dataset are presented below. Since the 3D modalities and the 7 poses are considered for the dictionary, it contains 8 dictionary blocks (see FIGS. 4A-4B). Furthermore, K-SVD was applied to create a compact dictionary $\tilde{D} \in R^{8800 \times 400}$ For testing, 2D images of expressions performed at the 7 pose angles are used. FIG. 4D provides an example of the sparse coefficients vectors extracted from a given subject performing a specific expression at multiple poses. In this figure one can observe many sparse coefficients that are present throughout all of the poses (red arrows), thus illustrating that the learned dictionary is invariant to observed poses. Furthermore since it is assumed that the sparse coefficient vector is approximately the same given any modality from a sample, then a given sample can be projected to modalities that may not have been observed (e.g., projecting a posed image to one containing 3D features).

An approach described herein achieved high results for pose-invariant FER, achieving 82% and 85% recognition rates when Neutral is and is not considered. In Table 1, results are compared to those of two recently published, state of the art methods, namely a pose-invariant method involving only 2D modalities [10] and a 3D specific method that only considers frontal face scans [13]. It should be noted the testing setup differed between cited methods. Rudovic et al. [10] provide results using manually annotated facial landmarks, and test on a wide variety of poses unseen to the training data including pitch poses. Zhao et al. [13] only consider 3D face scans, frontal pose, and do not classify the Neutral expression. With this said, our proposed approach therefore achieves results for FER that are on par with current state of the art approaches on the BU3D-FE dataset in a more general and challenging setting. When not including the (challenging) Neutral expression, the same recognition rate are achieved as [13] even though they only use the frontal pose and 3D data for testing.

TABLE 2

Comparisons of recognition rates for all expressions across the 7 poses on the MultiPie dataset. Our proposed method performs consistently well across drastic pose changes and significantly outperforms the baseline at server pose angles.

| Pose (deg) | −45 | −30 | −15 | 0 | 15 | 30 | 45 |
|---|---|---|---|---|---|---|---|
| Baseline | 67 | 76 | 90 | 91 | 91 | 75 | 64 |
| Proposed | 86 | 87 | 90 | 92 | 90 | 88 | 85 |

Table 2: Comparisons of recognition rates for all expressions across the 7 poses on the MultiPie dataset. Our proposed method performs consistently well across drastic pose changes and significantly outperforms the baseline at sever pose angles.

An experiment that utilizes both the BU3D-FE and MultiPie datasets are presented below, in order to validate the robustness of an approach described herein. First, a cross-modal and pose-invariant dictionary with the textured 3D data provided by the BU3D-FE dataset is learnt. Then using the 2D images from the MultiPie dataset, a FER classifier is tested and trained. Furthermore, the power of the proposed dictionary formulation is demonstrated by learning pose-invariant FER classification models using only frontal faces from the MultiPie dataset as training samples and testing on posed 2D images from the MultiPie dataset. This is the first instance where both of these datasets are utilized simultaneously and in this fashion. Although the expressions presented in the MultiPie dataset are only a subset of those presented in the BU3D-FE dataset, a pose-invariant dictionary is trained based on the entire BU3D-FE at the 7 dynamic pose angles to demonstrate our approach's general usability. Similar to the experiments in Section 3.2, K-SVD is applied to get a final pose-invariant dictionary $\tilde{D} \in R^{8800 \times 400}$. Five-fold cross validation is carried out on the MultiPie dataset, where at each fold 80% of the MultiPie subjects are used to train a classifier and the other 20% of the subjects at 7 different poses are used for testing. The dictionary learned from the BU3D-FE dataset did not change throughout any of the folds.

Table 2 shows the total recognition rates for all expressions across each of the 7 poses for a proposed method described herein and a baseline method. The baseline method consisted of training a multi-class SVM for each of the expressions performed on a frontal pose using the same set of 2D features as in Section 3.1. Both methods perform very well for nearly frontal faces when the pose is between −15 and 15 degrees; however outside this range, as severe pose changes occur, the proposed method greatly outperforms the baseline method and achieves high recognition rates similar to those of nearly frontal faces.

An example framework for constructing and learning a cross-modality and pose-invariant dictionary for the task of facial expression recognition has been described. Using the BU3D-FE dataset, results on par with current (frontal) state of the art approaches for 3D and pose-invariant expression recognition are presented. Furthermore, the robustness of such an approach has been presented by achieving high performance when two different datasets are combined. Furthermore, the generic nature of such an approach allows for many extensions including the use of different features and modalities.

It will be appreciated that the approaches, methods, techniques, and/or steps described above with regard to FIGS. 4A-4D are for illustrative purposes and that different and/or approaches, methods, techniques, and/or steps may be used for identifying facial expressions and/or determining behavioral assessments.

Figure 5:
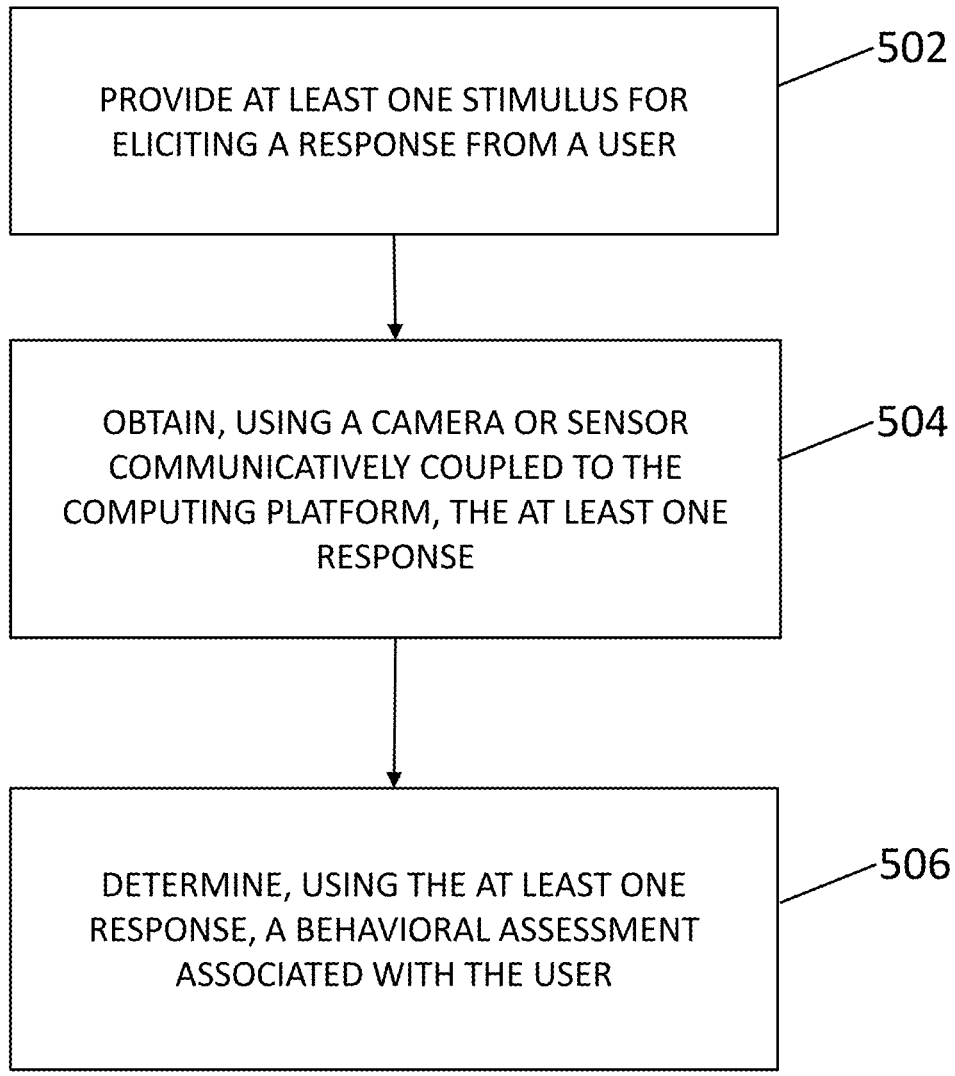
FIG. 5 is a diagram illustrating an exemplary process for automated behavioral assessment according to an embodiment of the subject matter described herein.

FIG. 5 is a diagram illustrating a process 500 for automated behavioral assessment according to an embodiment of the subject matter described herein. In some embodiments, process 500 described herein, or portions thereof, may be performed at or by computing platform 100, BAM 104, and/or another module or node. For example, computing platform 100 may be a mobile device, a computer, or other equipment (e.g., a computerized chair or room) and BAM 104 may include or provide an application running or executing on computing platform 100. In some embodiments, process 500 may include steps 502-506.

In step 502, at least one stimulus may be provided for eliciting a response from a user. For example, a video segment designed to illicit a user's eye movement from left to right or a certain emotion reflected via facial expressions may be provided to the user via user interface 110 (e.g., a display screen) of computing platform 100 (e.g., a smartphone).

In some embodiments, at least one stimulus may be generated for eliciting at least one response from a user based on historical information, psychological information, clinical information, personal information, or any combination thereof.

In some embodiments, at least one stimulus may include a video, an image, text, a sound, a color, or any combination thereof. For example, BAM 104 may provide video clips, audio clips, text (e.g., a questionnaire), or other stimuli to a user.

In some embodiments, providing at least one stimulus for eliciting at least one response from the user may include utilizing a stimuli-feedback loop involving different, additional, or dynamic stimuli based on one or more prior user responses. For example, various techniques (e.g., game mechanics and/or adaptive assessment model 200) may be used in providing dynamic stimuli to more accurate assess and/or code behaviors associated with user responses.

In step 504, the at least one response may be obtained, using a camera or sensor communicatively coupled to the computing platform. For example, BAM 104 may trigger camera/sensor 112 to record user responses while a video clip is provided to the user via user interface 110. In another example, camera/sensor 112 may represent a motion sensor or gyroscope sensor for recording a user's motions, e.g., a user moving with computing platform 100.

In some embodiments, camera/sensor 112 communicatively coupled to computing platform 100 may include a two dimensional camera, a three dimensional camera, a heat-sensor camera, and infrared camera, a gyroscope sensor, a motion sensor, a light sensor, or any combination thereof.

In some embodiments, at least one response may include a facial expression, a tongue movement, a facial movement, an eye movement, a vocal response, a heartrate change, blinking, blushing, a behavioral response, an emotional response, a physical responsive, a response delay, a lack of response, or any combination thereof.

In step 506, a behavioral assessment associated with the user may be determined using the at least one response. In some embodiments, a behavioral assessment may include a behavioral coding, a mental health screening or diagnosis, an autism diagnosis, an attention deficit hyperactivity disorder (ADHD), an anxiety disorder diagnosis, an aggressiveness disorder diagnosis, an indicator indicating a likelihood of a behavioral disorder, a score or weight associated with the at least one stimulus or the at least one response, a recommendation, a referral to a service provider, a mental health related report, or any combination thereof. For example, after analyzing one or more responses from a user, BAM 104 may generate and provide a behavioral assessment including information about potentially relevant behavioral disorders and/or suggestions for alleviating and/or improving any symptoms associated with potentially relevant behavioral disorders. In another example, a behavioral assessment may indicate the likelihood of a user being affected by one or more behavioral disorders.

In some embodiments, a behavioral assessment or related data may be provided to a user, a medical records system, a service provider, a healthcare provider, a caregiver of the user, or any combination thereof. For example, where information is provided to a clinician or a medical professional, a behavioral assessment may include stimuli used in a test, recording of the user during the test, test results, and/or other technical or clinical information. In another example, where information is provided to a parent, a behavioral assessment may include a metric associated with an easy to understand scale (e.g., 0-100%) for indicating the likelihood of a user (e.g., a child) having a particular behavioral disorder and useful suggestions for improving one or more related symptoms associated with behavioral disorder.

In some embodiments, follow-up information may be provided for contacting a service provider. In some embodiments, the follow-up information may include a list of service providers, a hyperlink associated with a service provider, an email address associated with a service provider, a chat identifier associated with a service provider, a telephone number associated with a service provider, a name associated with a service provider, an address associated with a service provider, a website associated with a service provider, or any combination thereof. For example, after providing a behavioral assessment to a user, BAM 104 may provide follow-up information via user interface 110. In this example, the follow-up information may include information usable for video chatting (e.g., via FaceTime®) with a healthcare worker, such as a doctor, nurse, or therapist.

In some embodiments, determining, using at least one response, a behavioral assessment associated with a user may include determining, by comparing the at least one response from the user to at least one baseline response associated with at least one stimulus, whether the at least one response from the user is indicative of a behavioral disorder.

In some embodiments, comparing at least one response from a user to at least one baseline response associated with at least one stimulus may include measuring a response delay between when the at least one stimulus is provided and when the at least one response from the user is detected and determining, using a baseline response delay indicative of normal behavior, whether the response delay meets or exceeds an assessment threshold indicative of a behavioral disorder.

In some embodiments, an assessment threshold may be based on a statistically significant deviation of a baseline response delay. For example, an assessment threshold may be determined using subject specific information (e.g., based on characteristics of the user) or population related information (e.g., based on a group of users with some similar characteristics, such as age, sex, knowledge, and skills). In this example, "statistically significant" may be a percentage above or below a mean or average response delay from subjects known to not have any behavioral disorders.

In some embodiments, computing platform 100 may include a mobile device, a smartphone, a tablet computer, a laptop computer, a computer, a behavioral assessment device, or a medical device.

It will be appreciated that process 500 is for illustrative purposes and that different and/or additional actions may be used. It will also be appreciated that various actions described herein may occur in a different order or sequence.

It should be noted that computing platform 100, BAM 104, and/or functionality described herein may constitute a special purpose computing device. Further, computing platform 100, BAM 104, and/or functionality described herein can improve the technological field of diagnosing and treating various behavioral disorders by providing mechanisms for automated behavior assessments. Moreover, such mechanisms can alleviate many barriers, including costs, equipment, and human expertise, associated with conventional (e.g., clinical) methods of diagnosis and treatment of behavioral disorders, e.g., in young children ranging from about 1 to 5 years of age.

The subject matter described herein for automated behavioral assessment improves the functionality of behavioral assessment devices and equipment by providing mechanisms for automatically providing stimuli, recording responses, and analyzing (e.g., coding) responses for determining whether user responses are indicative of one or more behavioral disorders. It should also be noted that computing platform 100 that implements subject matter described herein may comprise a special purpose computing device usable for automated various aspects of behavioral assessments, including stimuli selection and/or response analysis or coding.

The disclosure of each of the following references is incorporated herein by reference in its entirety to the extent not inconsistent herewith and to the extent that it supplements, explains, provides a background for, or teaches methods, techniques, and/or systems employed herein.

REFERENCES

[1] C. Nichols, L. Ibanez, J. Foss-Feig, and W. Stone, "Social smiling and its components in high-risk infant siblings without later asd symptomatology," JADD, vol. 44, no. 4, pp. 984-902, 2014.
[2] S. Ozonoff, A. Iosif, F. Baguio, I. Cook, M. Hill, T. Hutman, Rozga A. Roger, S., S. Sangha, M. Sigman, M. Steinfeld, and G. Young, "A prospective study of the emergence of early behavioral signs of autism a prospective study of the emergence of early behavioral signs of autism," J Am Acad Child Adolesc Psychiatry, vol. 49, no. 3, pp. 256-266, 2010.
[3] J. Rehg, G. Abowd, A. Rozga, M. Romero, M. Clements, S. Sclaroff, I. Essa, O. Ousley, L. Yin, K. Chanho, H. Rao, J. Kim, L. Presti, Z. Jianming, D. Lantsman, J. Bidwell, and Y Zhefan, "Decoding children's social behavior," in CVPR, 2013, pp. 3414-3421.
[4] J. Hashemi, M. Tepper, T. Spina, A. Esler, V. Morellas, N. Papanikolopoulos, H. Egger, G. Dawson, and G. Sapiro, "Computer vision tools for low-cost and non-invasive measurement of autism-related behaviors in infants," Autism Research and Treatment, 2014.
[5] C. Shan, S. Gong, and P. McOwan, "Facial expression recognition based on local binary patterns: a comprehensive study," in Image and Vision Computing, 2009, vol. 27, pp. 803-816.
[6] Z. Zeng, M. Pantic, G. Roisman, and T. Huang, "A survey of affect recognition methods: audio, visual, and spontaneous expressions," in PAMI, 2009, vol. 31, pp. 39-58.
[7] Z. Zhu and Q. Ji, "Robust real-time face pose and facial expression recovery," in CVPR, 2006, pp. 681-688.
[8] S. Moore and R. Bowden, "Local binary patterns for Multiview facial expression recognition," in Computer Vision and Image Understanding, 2011, vol. 115, pp. 541-558.
[9] H. Tang, M. Hasegawa-Johnson, and T. Huang, "Non-frontal view facial expression recognition based on ergodic hidden markov model supervectors," in ICME, 2010, pp. 1202-1207.
[10] O. Rudovic, M. Pantic, and I. Patras, "Coupled Gaussian processes for pose-invariant facial expression recognition," PAMI, vol. 35, no. 6, pp. 1357 1369, 2013.
[11] S. Kumano, K. Otsuka, J. Yamato, E. Maeda, and Y. Sato, "Pose-invariant facial expression recognition using variable intensity templates," IJVC, vol. 83, no. 2, pp. 178-194, 2009.
[12] F. Guney, N. Arar, M. Fischer, and H. Ekenel, "Cross-pose facial expression recognition," FG, pp. 1-6, 2013.
[13] X. Zhao, E. Dellandr'ea, and J. Zou, "A unified probabilistic framework for automatic 3D facial expression analysis based on a bayesian belief inference and statistical feature models," Image and Vision Computing, vol. 31, no. 3, pp. 231-245, 2013.
[14] G. Sandbach, S. Zafeiriou, M. Pantic, and L. Yin, "Static and dynamic 3D facial expression recognition: a comprehensive survey," Image and Vision Computing, vol. 30, no. 10, pp. 683-697, 2012.
[15] S. Taheri, Q. Qiu, and R. Chellappa, "Structure-preserving sparse decomposition for facial expression analysis," IEEE Trans Image Process, vol. 23, no. 8, pp. 3590-3603, 2014.
[16] J. Wright, A. Yang, A. Ganesh, S. Sastry, and Yi. Ma, "Robust face recognition via sparse representation," PAMI, vol. 31, no. 2, pp. 210-227, 2009.
[17] T. Hastie, R. Tibshirani, and J. Friedman, The Elements of Statistical Learning, Springer-Verlag, 2001.
[18] Q. Qiu, V. Patel, P. Turaga, and R. Chellappa, "Domain adaptive dictionary learning," in ECCV, 2012, pp. 631-645.
[19] L. Yin, X. Wei, J. Wang, and M. Rosato, "A 3D facial expression database for facial behavior research," in FG, 2006, pp. 211-216.
[20] R. Gross, I. Matthews, J. Cohn, T. Kanade, and S. Baker, "Multi-PIE," in FG, 2010, pp. 807-813.
[21] M. Aharon, M. Elad, and A. Bruckstein, "K-SVD: an algorithm for designing overcomplete dictionaries for sparse representation," IEEE Trans Signal Process, vol. 54, no. 11, pp. 4311-4322, 2006.
[22] E. Chutorian and M. Trivedi, "Head pose estimation in computer vision: a survey," PAMI, vol. 31, no. 4, pp. 607-626, 2009.
[23] X. Xiong and F. De la Torre, "Supervised descent method and its applications to face alignment," in CVPR, 2013, pp. 532-539.
[24] C. Chang and C. Lin, "LIBSVM: a library for support vector machines," ACM Trans Intelligent Systems and Technology, vol. 2, no. 3, pp. 1-27, 2011.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:
1. A method for automated behavioral assessment, the method comprising:
at a computing platform including a processor and memory:
identifying skills and risk factors associated with a user based on user interactions;
providing at least one stimulus for eliciting at least one response from the user, wherein the at least one stimulus includes a first stimulus determined using the skills and the risk factors associated with the user, wherein the at least one stimulus includes an assessment video containing a non-social component and a social component;
obtaining, using a camera or sensor communicatively coupled to the computing platform, at least one response, wherein the camera or sensor records the at least one response from the user; and
determining, using the at least one response, a behavioral assessment associated with the user, wherein determining the behavioral assessment associated with the user includes analyzing video of the user for determining whether the at least one response is indicative of a behavioral disorder, wherein analyzing the video of the user comprises:

identifying, using a response recognition algorithm, a facial area using identifiable facial landmarks at various angles and/or head positions;

detecting changes to the identified facial area using the response recognition algorithm, wherein detecting changes includes detecting an amount of time the user spent attending to the non-social component or the social component of the assessment video, wherein detecting changes includes analyzing, using a pose-invariant dictionary, the at least one response to identify one or more facial expressions of the user during the at least one response, wherein the pose-invariant dictionary contains three dimensional (3D) shape and morphological information derived from a first dataset and two dimensional (2D) texture and geometric information derived from a second dataset, wherein the pose-invariant dictionary contains 3D features for a plurality of subjects and 2D features based on synthesized head poses for the plurality of subjects; and determining, based on the changes, that the at least one response is indicative of a behavioral disorder, wherein determining that the at least one response is indicative of the behavioral disorder includes determining, by comparing the at least one response from the user to at least one baseline response associated with the at least one stimulus, that the at least one response from the user is indicative of the behavioral disorder, wherein comparing the at least one response from the user to at least one baseline response associated with the at least one stimulus includes determining that the amount of time the user spent attending to the non-social component or the social component meets or exceeds an assessment threshold indicative of the behavior disorder, wherein comparing the at least one response from the user to at least one baseline response associated with the at least one stimulus includes detecting a user's lack of expressiveness as compared to an expressiveness baseline, wherein comparing the at least one response from the user to at least one baseline response associated with the at least one stimulus includes:

measuring a first response delay between when a video-based non-social stimulus of the at least one stimulus is provided and when a first response of the at least one response from the user is detected, determining, using a first baseline response delay indicative of normal behavior associated with the video-based non-social stimulus, whether the first response delay meets or exceeds a second assessment threshold indicative of the behavioral disorder, measuring a second response delay between when a video-based social stimulus of the at least one stimulus is provided and when a second response of the at least one response from the user is detected, and determining, using a second baseline response delay indicative of normal behavior associated with the video-based social stimulus, whether the second response delay meets or exceeds a third assessment threshold indicative of the behavioral disorder, wherein the first baseline response delay is different from the second baseline response delay and wherein the second assessment threshold is different from the third assessment threshold.

2. The method of claim 1 comprising:

providing the behavioral assessment or related data to the user, a medical records system, a service provider, a healthcare provider, a caregiver of the user, or any combination thereof; or providing follow-up information for contacting a service provider, wherein the follow-up information may include a list of service providers, a hyperlink associated with a service provider, an email address associated with a service provider, a chat identifier associated with a service provider, a phone number associated with a service provider, a name associated with a service provider, an address associated with a service provider, a website associated with a service provider, or any combination thereof.

3. The method of claim 1 wherein the at least one stimulus includes game mechanics, a video, an image, text, a sound, a color, or any combination thereof.

4. The method of claim 1 wherein the at least one stimulus is associated with one or more baseline responses for comparison to the at least one response from the user.

5. The method of claim 1 wherein the at least one stimulus is generated for eliciting the at least one response from the user based on historical information, psychological information, clinical information, personal information, or any combination thereof.

6. The method of claim 1 wherein the at least one response includes a facial expression, a tongue movement, a facial movement, an eye movement, a vocal response, a heartrate change, blinking, blushing, a behavioral response, an emotional response, a physical response, a response delay, a lack of response, or any combination thereof.

7. The method of claim 1 wherein providing the at least one stimulus for eliciting the at least one response from the user includes utilizing a stimuli-feedback loop involving different, additional, or dynamic stimuli based on one or more prior user responses.

8. The method of claim 1 wherein the camera or sensor includes a two dimensional camera, a three dimensional camera, a heat-sensor camera, an infrared camera, a gyroscope sensor, a motion sensor, a light sensor, or any combination thereof.

9. The method of claim 1 wherein the behavioral assessment includes a behavioral coding, a mental health screening or diagnosis, an autism diagnosis, an attention deficit hyperactivity disorder (ADHD), an anxiety disorder diagnosis, an aggressiveness disorder diagnosis, an indicator indicating a likelihood of the behavioral disorder, a score or weight associated with the at least one stimulus or the at least one response, a recommendation, a referral to a service provider, a mental health related report, or any combination thereof.

10. The method of claim 1 wherein the third assessment threshold is based on a statistically significant deviation of the second baseline response delay.

11. The method of claim 1 wherein the computing platform includes a mobile device, a smartphone, a tablet computer, a laptop computer, a computer, a behavioral assessment device, or a medical device.

12. A system for automated behavioral assessment, the system comprising:

a computing platform including a processor and memory, the computing platform including:

a behavioral assessment module (BAM) implemented using the processor and the memory configured to identify skills and risk factors associated with a user based on user interactions; to provide at least one stimulus for eliciting at least one response from the user, wherein the at least one stimulus includes a first stimulus determined using the skills and the risk factors associated with the user, wherein the at least one stimulus includes an assessment video containing a non-social component and a social component; to obtain, using a camera or sensor communicatively coupled to the computing platform, at least one response, wherein the camera or sensor records the at least one response from the user; and to determine, using the at least one response, a behavioral assessment associated with the user, wherein determining the behavioral assessment associated with the user includes analyzing video of the user for determining whether the at least one response is indicative of a behavioral disorder, wherein analyzing the video of the user comprises:

identifying, using a response recognition algorithm, a facial area using identifiable facial landmarks at various angles and/or head positions;

detecting changes to the identified facial area using the response recognition algorithm, wherein detecting changes includes detecting an amount of time the user spent attending to the non-social component or the social component of the assessment video, wherein detecting changes includes analyzing, using a pose-invariant dictionary, the at least one response to identify one or more facial expressions of the user during the at least one response, wherein the pose-invariant dictionary contains three dimensional (3D) shape and morphological information derived from a first dataset and two dimensional (2D) texture and geometric information derived from a second dataset, wherein the pose-invariant dictionary contains 3D features for a plurality of subjects and 2D features based on synthesized head poses for the plurality of subjects; and determining, based on the changes, that the at least one response is indicative of a behavioral disorder, wherein determining that the at least one response is indicative of the behavioral disorder includes determining, by comparing the at least one response from the user to at least one baseline response associated with the at least one stimulus, that the at least one response from the user is indicative of the behavioral disorder, wherein comparing the at least one response from the user to at least one baseline response associated with the at least one stimulus includes determining that the amount of time the user spent attending to the non-social component or the social component meets or exceeds an assessment threshold indicative of the behavior disorder, wherein comparing the at least one response from the user to at least one baseline response associated with the at least one stimulus includes detecting a user's lack of expressiveness as compared to an expressiveness baseline, wherein comparing the at least one response from the user to at least one baseline response associated with the at least one stimulus includes:

measuring a first response delay between when a video-based non-social stimulus of the at least one stimulus is provided and when a first response of the at least one response from the user is detected, determining, using a first baseline response delay indicative of normal behavior associated with the video-based non-social stimulus, whether the first response delay meets or exceeds a second assessment threshold indicative of the behavioral disorder, measuring a second response delay between when a video-based social stimulus of the at least one stimulus is provided and when a second response of the at least one response from the user is detected, and determining, using a second baseline response delay indicative of normal behavior associated with the video-based social stimulus, whether the second response delay meets or exceeds a third assessment threshold indicative of the behavioral disorder, wherein the first baseline response delay is different from the second baseline response delay and wherein the second assessment threshold is different from the third assessment threshold.

13. The system of claim 12 wherein the BAM is configured to provide the behavioral assessment or related data to the user, a medical records system, a healthcare provider, a caregiver of the user, or any combination thereof; or to provide follow-up information for contacting a service provider, wherein the follow-up information may include a list of service providers, a hyperlink associated with a service provider, an email address associated with a service provider, a chat identifier associated with a service provider, a phone number associated with a service provider, a name associated with a service provider, an address associated with a service provider, a website associated with a service provider, or any combination thereof.

14. The system of claim 12 wherein the at least one stimulus includes game mechanics, a video, an image, text, a sound, a color, or any combination thereof.

15. The system of claim 12 wherein the at least one stimulus is associated with one or more baseline responses for comparison to the at least one response from the user.

16. The system of claim 12 wherein the BAM is configured to generate the at least one stimulus for eliciting the at least one response from the user based on historical information, psychological information, clinical information, personal information, or any combination thereof.

17. The system of claim 12 wherein the at least one response includes a facial expression, a tongue movement, a facial movement, an eye movement, a vocal response, a heartrate change, blinking, blushing, a behavioral response, an emotional response, a physical response, a response delay, a lack of response, or any combination thereof.

18. The system of claim 12 wherein the BAM is configured to utilize a stimuli-feedback loop involving different, additional, or dynamic stimuli based on one or more prior user responses.

19. The system of claim 12 wherein the camera or sensor includes a two dimensional camera, a three dimensional camera, a heat-sensor camera, an infrared camera, a gyroscope sensor, a motion sensor, a light sensor, or any combination thereof.

20. The system of claim 12 wherein the behavioral assessment includes a behavioral coding, a mental health screening or diagnosis, an autism diagnosis, an attention deficit hyperactivity disorder (ADHD), an anxiety disorder diagnosis, an aggressiveness disorder diagnosis, an indicator indicating a likelihood of the behavioral disorder, a score or weight associated with the at least one stimulus or the at least one response, a recommendation, a mental health related report, or any combination thereof.

21. The system of claim 12 wherein the third assessment threshold is based on a statistically significant deviation of the second baseline response delay.

22. The system of claim 12 wherein the computing platform includes a mobile device, a smartphone, a tablet computer, a laptop computer, a computer, a behavioral assessment device, or a medical device.

23. A non-transitory computer readable medium comprising computer executable instructions embodied in a computer readable medium that when executed by a processor of a computer control the computer to perform steps comprising:

at a computing platform including a processor and memory, the computing platform including:
identifying skills and risk factors associated with a user based on user interactions;
providing at least one stimulus for eliciting at least one response from the user, wherein the at least one stimulus includes a first stimulus determined using the skills and the risk factors associated with the user, wherein the at least one stimulus includes an assessment video containing a non-social component and a social component;
obtaining, using a camera or sensor communicatively coupled to the computing platform, at least one response, wherein the camera or sensor records the at least one response from the user; and
determining, using the at least one response, a behavioral assessment associated with the user, wherein determining the behavioral assessment associated with the user includes analyzing video of the user for determining whether the at least one response is indicative of a behavioral disorder, wherein analyzing the video of the user comprises:
identifying, using a response recognition algorithm, a facial area using identifiable facial landmarks at various angles and/or head positions;
detecting changes to the identified facial area using the response recognition algorithm, wherein detecting changes includes detecting an amount of time the user spent attending to the non-social component or the social component of the assessment video, wherein detecting changes includes analyzing, using a pose-invariant dictionary, the at least one response to identify one or more facial expressions of the user during the at least one response, wherein the pose-invariant dictionary contains three dimensional (3D) shape and morphological information derived from a first dataset and two dimensional (2D) texture and geometric information derived from a second dataset, wherein the pose-invariant dictionary contains 3D features for a plurality of subjects and 2D features based on synthesized head poses for the plurality of subjects; and
determining, based on the changes, that the at least one response is indicative of a behavioral disorder, wherein determining that the at least one response is indicative of the behavioral disorder includes determining, by comparing the at least one response from the user to at least one baseline response associated with the at least one stimulus, that the at least one response from the user is indicative of the behavioral disorder, wherein comparing the at least one response from the user to at least one baseline response associated with the at least one stimulus includes determining that the amount of time the user spent attending to the non-social component or the social component meets or exceeds an assessment threshold indicative of the behavior disorder, wherein comparing the at least one response from the user to at least one baseline response associated with the at least one stimulus includes detecting a user's lack of expressiveness as compared to an expressiveness baseline, wherein comparing the at least one response from the user to at least one baseline response associated with the at least one stimulus includes:
measuring a first response delay between when a video-based non-social stimulus of the at least one stimulus is provided and when a first response of the at least one response from the user is detected,
determining, using a first baseline response delay indicative of normal behavior associated with the video-based non-social stimulus, whether the first response delay meets or exceeds a second assessment threshold indicative of the behavioral disorder,
measuring a second response delay between when a video-based social stimulus of the at least one stimulus is provided and when a second response of the at least one response from the user is detected, and
determining, using a second baseline response delay indicative of normal behavior associated with the video-based social stimulus, whether the second response delay meets or exceeds a third assessment threshold indicative of the behavioral disorder, wherein the first baseline response delay is different from the second baseline response delay and wherein the second assessment threshold is different from the third assessment threshold.

\* \* \* \* \*